United States Patent [19]

Loughrey et al.

[11] Patent Number: 5,059,421

[45] Date of Patent: Oct. 22, 1991

[54] PREPARATION OF TARGETED LIPOSOME SYSTEMS OF A DEFINED SIZE DISTRIBUTION

[75] Inventors: Helen C. Loughrey; Pieter R. Cullis, both of Vancouver; Marcel B. Bally, Bowen Island; Lewis S. L. Choi, Burnaby; Kim F. Wong, Vancouver, all of Canada

[73] Assignee: The Liposome Company, Inc., Princeton, N.J.

[21] Appl. No.: 370,650

[22] Filed: Jun. 23, 1989

Related U.S. Application Data

[63] Continuation-in-part of Ser. No. 941,913, Dec. 15, 1986, Pat. No. 4,885,172, which is a continuation-in-part of Ser. No. 811,037, Dec. 18, 1985, abandoned, which is a continuation-in-part of Ser. No. 749,161, Jun. 26, 1985, abandoned, which is a continuation-in-part of Ser. No. 759,419, Jul. 26, 1985, Pat. No. 4,880,635.

[51] Int. Cl.$^5$ ............... A01N 25/26; A01N 25/28; A61K 37/22; B32B 5/16
[52] U.S. Cl. ................... 424/417; 424/418; 424/450; 435/4; 264/4.3
[58] Field of Search .............. 424/417, 418, 450; 435/4; 264/4.3

[56] References Cited

U.S. PATENT DOCUMENTS

| | | |
|---|---|---|
| 4,193,983 | 3/1980 | Ullman et al. ............ 436/528 |
| 4,235,871 | 11/1980 | Papahadjopoulos et al. ...... 424/19 |
| 4,308,166 | 12/1981 | Marchetti et al. ............ 424/450 |
| 4,522,803 | 6/1985 | Lenk et al. ............ 424/1.1 |
| 4,588,578 | 5/1986 | Fountain et al. ............ 424/1.1 |
| 4,610,868 | 9/1986 | Fountain et al. ............ 424/1.1 |
| 4,721,612 | 1/1988 | Janoff et al. ............ 424/1.1 |
| 4,789,633 | 12/1988 | Huang et al. ............ 424/450 |
| 4,830,858 | 5/1989 | Payne et al. ............ 424/417 |
| 4,863,740 | 9/1989 | Kissel et al. ............ 424/450 |
| 4,873,088 | 10/1989 | Mayhew et al. ............ 424/450 |
| 4,877,561 | 10/1989 | Iga et al. ............ 264/4.3 |
| 4,880,635 | 11/1989 | Janoff et al. ............ 424/450 |
| 4,885,172 | 12/1989 | Bally et al. ............ 424/417 |

FOREIGN PATENT DOCUMENTS

WO86/00238 1/1986 World Int. Prop. O. .
WO87/02219 4/1987 World Int. Prop. O. .

OTHER PUBLICATIONS

Rahman et al., J. Cell. Biol., 83, p. 268a, 1979.
Cullis et al. U.S. patent application No. 622,690, filed 6/20/1984.
Bally et al. U.S. patent application No. 941,913, filed 12/15/86.
Bally et al. U.S. patent application No. 749,161, filed 6/26/85.
Janoff et al. U.S. patent application No. 759,419, file 7/26/85.
Leak et al. U.S. patent application No. 476,496, filed 3/24/83.
Fountain et al. U.S. patent application No. 521,176, filed 8/8/83.
Fountain U.S. patent application No. 591,576, filed 3/20/84.
Janoff et al. U.S. patent application No. 599,691, filed 4/12/84.

(List continued on next page.)

Primary Examiner—Ronald W. Griffin
Attorney, Agent, or Firm—Allen Bloom; Catherine Kurtz

[57] ABSTRACT

The present invention relates to a general method for producing sized protein-liposome conjugates exhibiting enhanced blood circulation times. The present invention also relates to the sized protein-liposome conjugate compositions produced by the method of the present invention. The protein-liposome conjugates of the present invention preferably range in size from about 75 nm to about 200 nm.

The liposomes of the invention may have a transmembrane potential across their membranes, and may be dehydrated. In addition, the composition may contain ionizable bioactive agents such as antineoplastic agents, and may be used in diagnostic assays.

68 Claims, 7 Drawing Sheets

OTHER PUBLICATIONS

Bally et al. U.S. patent application No. 811,037, filed 12/18/85.
Cullis et al. U.S. patent application No. 353,497, filed 5/15/89.
Allison et al., "Liposomes as Immunological Adjuvants," 1974, Nature, 252, p. 252.
Bangham et al., "Diffusion of Univalent Ions Across the Lamellae of Swollen Phospholipids," 1965, J. Mol. Biol. 13:238–252.
Brederhorst R. et al., "Effect of Covalent Attachment of Immunoglobulin Fragments on Liposomal Integrity," Biochem., 1986, 25:5693–5698.
Carlsson et al., "Protein Thiolation and Reversible Protein-Protein Conjugation" 1978, Biochem. J., 173:723–737.
Deamer et al., "Liposome Preparation: Methods and Mechanisms," 1983, Chaper 1, pp. 27–51.
Fiske et al., "The Colorimetric Determination of Phosphorus", 1925, J. Bio. Chem., vol. 66, No. 2:375–400.
Forssen et al., "Improved Therpeutic Benefits of Doxorubicin by Entrapment in Anionic Liposomes," 1983, Cancer Res., 43:546–550.
Gabizon et al., "Liposomes as in Vivo Carriers of Adriamycin: Reduced Cardiac Uptake and Preserved Antitumor Activity in Mice", 1982, Cancer Res., 42:4734–4739.
Goundalkar et al., "Covalent Binding of Antibodies to Lipsomes Using a Novel Lipid Derivative," 1984, J. Pharm. Pharmacol., 36:465–466.
Gregoriadis, "Targeting of Drugs with Molecules, Cells and Liposomes," 1983, Trends Pharmacol Sci., 4:304–307.
Heath et al., "Antibody-Targeting Liposomes: Increase in Specific Toxicity of Methotrexate-Y-Aspartate," 1983, Proc. Acad. Sci. USA, 80:1377–1381.
Heath et al., "Covalent Attachment of Immunogloublins in Liposomes Via Glycosphingolipids," 1981, Biochim. Biophys. Acta, 640:66–81.
Heath et al., "Covalent Attachment of Horseradish Peroxidase to the Outer Surface of Liposomes," 1980, Biochium. Biophys. Acta. 599:42–62.
Ho et al., "Interactions of Antigen-Sensitized Liposomes with Immobilized Antibody: A Homogeneous Solid-Phase Immunoliposome Assay," 1985, J. Immunol., vol. 134:4035–4040.
Hope et al., "Production of Large Unilamellar Vesicles by a Rapid Extrusion Procedure. Characterization of Size Distribution, Trapped Volume and Ability to Maintain a Membrane Potential", 1981, Biochim. Biophys. Acta., 812:55–65.
Huang L., "Liposome-Cell Interactions in Vitro", 1983, Liposomes, Ed. Marc J. Ostro by Marcel Dekker, New York, pp. 87–124.
Huang et al., "Characterization on Antibody Covalently Coupled to Liposomes," 1982, Biochim. Biophys. Acta., 716:140–150.
Huang et al., "Interactions of Immunoliposomes with Target Cells," 1983, J. Biol. Chem., 258, No. 22:14034–14040.
Hunt, A. C., "Liposomes Disposition In Vivo, V. Liposome Stability in Plasma and Implications for Drug Carrier Function," 1982, Biochim. Biophys. Acta., 719:450–463.
Ishimori et al., "Liposome Immune Lysis Assay (LILA): A Simple Method to Measure Anti-Protein Antibody Using Protein Antigen-Bearing Liposome," 1984, J. Immunol. Methods, 75:351–360.
Leserman et al., "Targeting to Cells of Fluorescent Liposomes Covalently Coupled with Monoclonal Antibody or Protein A," 1980, Nature, 288:602–604.
Leserman et al., "Covalent Coupling of Monoclonal Antibodies and Protein A to Liposomes: Specific Interaction with Cells in Vitro and in Vivo," Liposome Technology, III, 1984, CRC Press, Inc., CA., pp. 29–40.
Loughery et al., "A Non-Covalent Method of Attaching Antibodies to Liposomes," 1987, Biochim. Biophys. Acta., 901:157–160.
Martin et al., "Irreversible Coupling of Immunoglobulin Fragments to Preformed Vesicles," 1982, J. Biol. Chem., 257, pp. 286–288.
Martin et al., "Immunospecific Targeting of Liposomes to Cells: A Novel and Efficient Method for Covalent Attachment of Fab' Fragments via Disulfide Bonds," 1981, Biochemistry, 20:4229–4238.
Papahadjapoulos et al., "Phospholipid Model Membranes I. Structural Characteristics of Hydrated Liquid Crystals," 1967, Biochim. Biophys. Acta, 135:624–638.
Papahadjopoulos et al., "Targeting of Liposomes to Tumor Cells in Vivo," 1988, Annals of the N.Y. Academy of Sci., ed. R. L. Juliano, 507, 64–74.

(List continued on next page.)

OTHER PUBLICATIONS

Rahman et al., "In Vivo Cell Targeting by Liposomes Containing Glycolipids," 1979, J. Cell. Biol., MF1509.

Rahman et al., "Doxorubicin-Induced Chronic Cardiotoxicity and Its Protection by Liposomal Administration," 1982, Cancer Res. 42:1817-1825.

Sato et al., "Effects of Dose and Vesicle Size on the Pharmacokinetics of Liposomes," 1986, Chem. Pharm. Bull., 34:4244-4252.

Sharkey et al., "Targeting of Antibody Coated Liposomes to Tumor Cells Producing Carcinoembryonic Antigen", 1979, Fed. Proc., 38, 1089, #4557.

Stein et al., "Biological Stability of [$^3$H] Cholesteryl Oleyl Ether in Cultured Firbroblasts and Intact Rat," 1980, Febs Lett., vol. 111: 104-106.

Urdal et al., J. Biol. Chem., "Tumor-Associated Ganglio-N-Triosylceramide", 1984, J. Biol. Chem., 255:10509-10516.

Wolff et al., "The Use of Monoclonal Anti-Thy, $IgG_{,1}$" for the Targeting of Liposomes to AKR-A Cells In Vitro aned In Vivo, 1984, Biochim Biophys. Acta., 802:259-273.

FIG. 2A
FIG. 2B
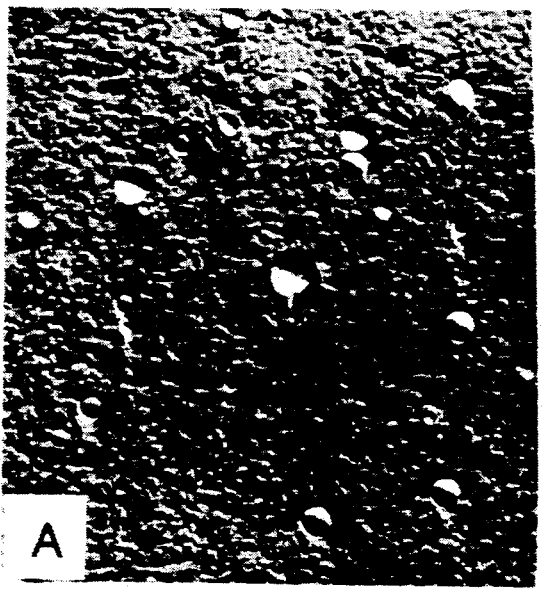
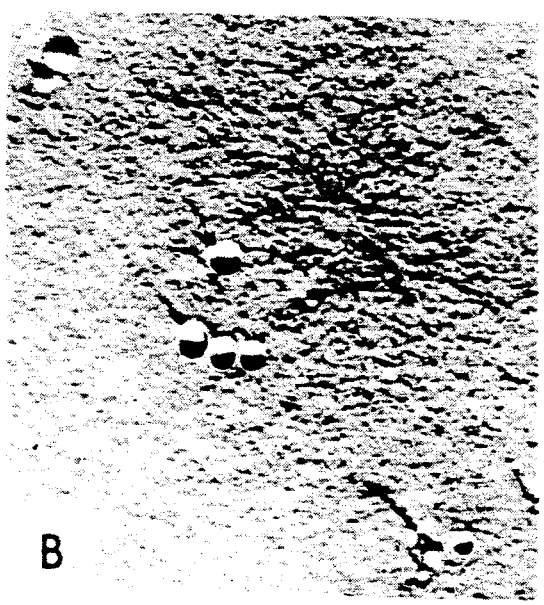
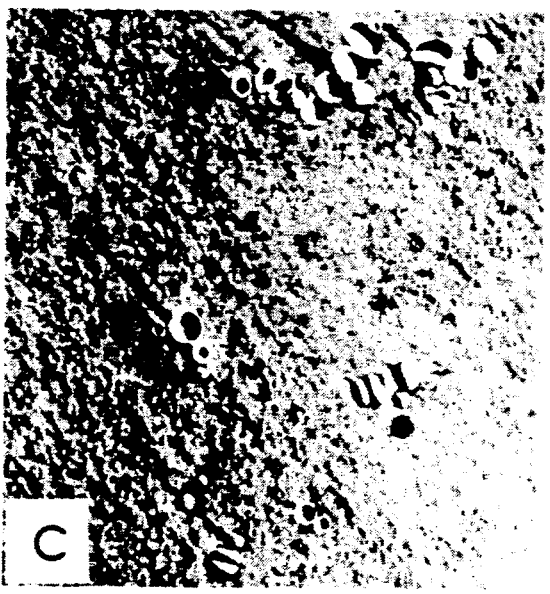
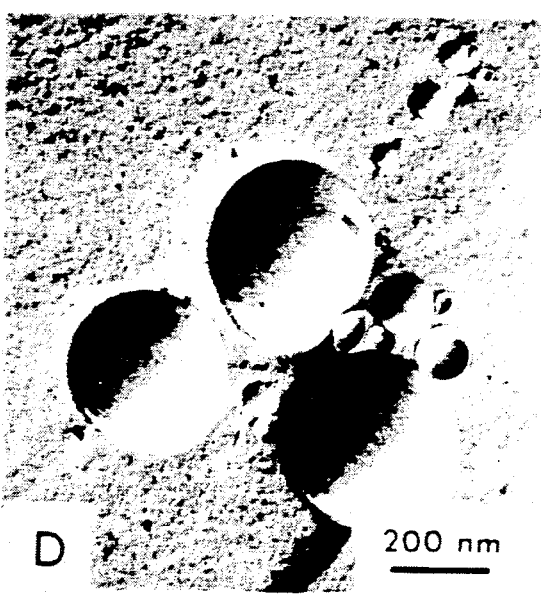
FIG. 2C
FIG. 2D

FIG. 5A
FIG. 5B
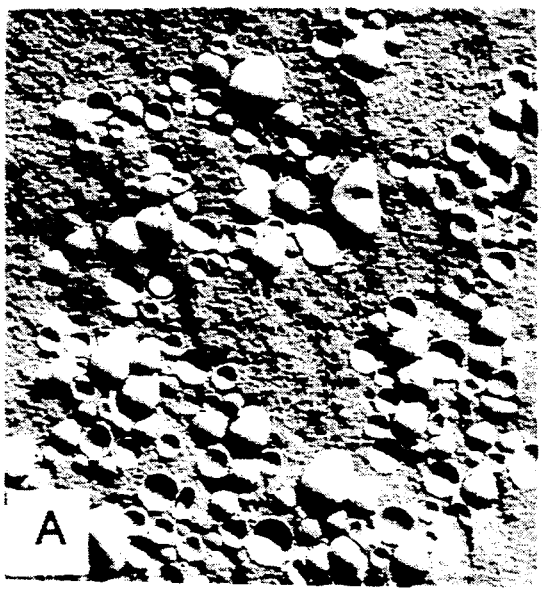
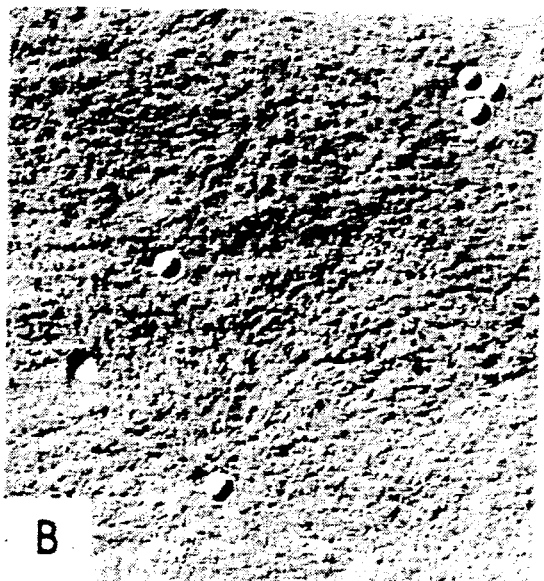
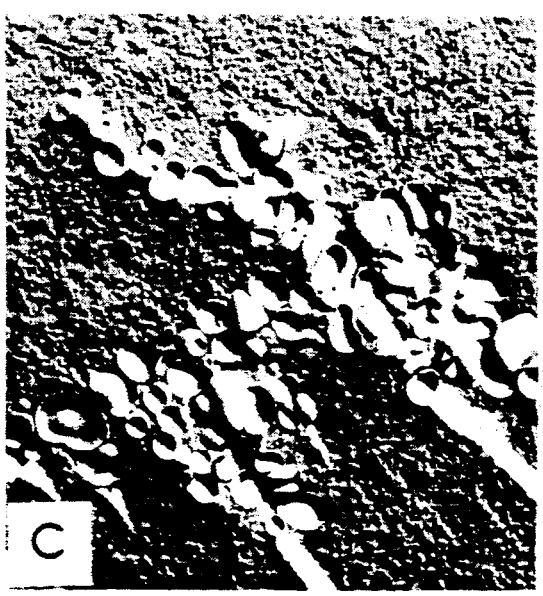
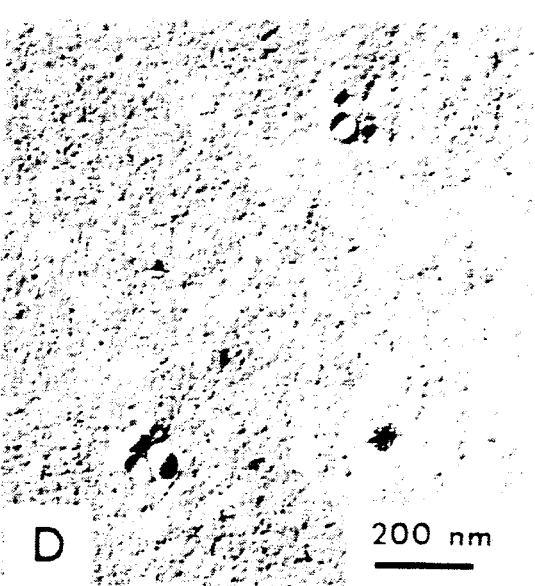
FIG. 5C
FIG. 5D

PREPARATION OF TARGETED LIPOSOME SYSTEMS OF A DEFINED SIZE DISTRIBUTION

This is a continuation-in-part application of copending which is a continuation-in-part application of patent application Ser. No. 811,037, filed Dec. 18, 1985, which is a continuation-in-part application of patent application Ser. No. 749,161, filed June 26, 1985, and patent application Ser. No. 759,419, filed July 26, 1985.

FIELD OF THE INVENTION

The present invention relates to a general method for producing sized protein-liposome conjugates exhibiting enhanced blood circulation times. The present invention also relates to sized protein-liposome conjugate compositions produced by the method of the present invention. The conjugates of the present invention preferably range in size from about 30 nm to about 150 nm and exhibit favorable blood circulation times.

Protein-liposome conjugates of the present invention may be used for targetting the delivery of an active agent in vivo or in diagnostics.

Protein-liposome conjugates of the present invention may have a transmembrane potential across their membranes, and may be dehydrated. In addition, the conjugates may contain ionizable bioactive agents, for example antineoplastic agents, and may be used in diagnostic assays.

BACKGROUND OF THE INVENTION

Liposomes are completely closed structures comprising lipid bilayer membranes containing an encapsulated aqueous volume. Liposomes may contain many concentric lipid bilayers separated by an aqueous phase (multilamellar vesicles or MLVs), or alternatively, they may comprise a single membrane bilayer (unilamellar vesicles). The lipid bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase. The basic structure of liposomes may be made by a variety of techniques known in the art.

Liposomes have typically been prepared using the process of Bangham et al., (1965 J. Mol. Biol., 13: 238-252), whereby lipids suspended in organic solvent are evaporated under reduced pressure to a dry film in a reaction vessel. An appropriate amount of aqueous phase is then added to the vessel and the mixture agitated. The mixture is then allowed to stand, essentially undisturbed for a time sufficient for the multilamellar vesicles to form. The aqueous phase entrapped within the liposomes may contain bioactive agents, for example drugs, hormones, proteins, dyes, vitamins, or imaging agents, among others.

Liposomes may be reproducibly prepared using a number of currently available techniques. The types of liposomes which may be produced using a number of these techniques include small unilamellar vesicles (SUVs) [See Papahadjapoulous and Miller, Biochem. Biophys. Acta., 135, p. 624-638 (1967)], reverse-phase evaporation vesicles (REV) [See U.S. Pat. No. 4,235,871 issued Nov. 25, 1980], stable plurilamellar vesicles (SPLV) [See U.S. Pat. No. 4,522,803, issued June 11, 1985], and large unilamellar vesicles produced by an extrusion technique as described in copending U.S. patent application Ser. No. 622,690, filed June 20, 1984, Cullis et.al., entitled "Extrusion Technique for Producing Unilamellar Vesicles", relevant portions of which are incorporated herein by reference.

Liposomes may be used as carriers for a wide variety of materials, for example drugs, cosmetics, diagnostic reagents and bioactive compounds, among others. Liposome compositions to which proteins are conjugated may be designed for both diagnostic and in vivo uses. For example, the ability to produce an antibody-directed vesicle would be a distinct advantage over similar undirected systems (Gregoriadis, G., Trends Pharmacol Sci, 4, p. 304-307, 1983), as would the targetting of a specific receptor or other cell surface feature. Useful applications of these protein-liposome conjugates would be in the selective targeting of cytotoxic compounds entrapped in vesicles to circulating tumor cells (Wolff et.al., Biochim. Biophys. Acta, 802, p. 259-273 1984), or applications of these immunoglobulin-associated vesicles in the development of diagnostic assays. Further applications could result from the targeting of a specific protein-receptor interaction for delivery of active agent to a specific site in a patient. Indeed, protein conjugated liposomes theoretically could be used to target the delivery of any active agent to a site in the patient's system to which the protein will bind. Numerous techniques for the conjugation of proteins to liposomes have already been developed for a variety of purposes including the targeting of drugs via immunoliposomes [See Leserman, et al., Nature. 288, 602 (1980), Heath, et al., Proc. Natl. Acad. Sci. USA, 80, 1377 (1983) and Huang, et al., J. Biol. Chem., 258, 14034 (1983)], diagnostic protocols [See Ishimori, et al., J. Immunol. Methods, 75, 351 (1984) and Ho, et al., J. Immunol.. 134, 4035 (1985)]and liposomal vaccines [See Allison, et al., Nature, 252, 252 (1974)].

Liposomes may be covalently coupled to proteins, antibodies and immunoglobins. Heath et.al. (Biochim. Biophys. Acta., 640, p. 66-81, 1981), describe the covalent attachment of immunoglobulins to liposomes containing glycosphingolipid. Leserman et. al. (Liposome Technology, III, 1984, CRC Press, Inc., CA., p. 29-40; Nature, 288, p. 602-604, 1980) and Martin et. al., (J. Biol. Chem., 257, p. 286-288, 1982) have described procedures whereby thiolated IgG or protein A is covalently attached to lipid vesicles, and thiolated antibodies and Fab' fragments are attached to liposomes, respectively. These protocols and various modifications (Martin et.al, Biochemistry, 20, p. 4229-4238, 1981; and Goundalkar et.al. J Pharm. Pharmacol., 36, p. 465-466, 1984) represent the most versatile approaches to coupling. Avidin-coupled and avidin and biotinylcoupled phospholid liposomes containing actinomycin D have successfully targeted tumor cells expressing ganglio-Ntriosylceramide (Urdal et.al., J. Biol. Chem., 255, p. 10509-10516, 1980). Huang et.al. (Biochim. Biophys. Acta.. 716, p. 140-150, 1982) demonstrate the binding of mouse monoclonal antibody to the major histocompatibility antigen H-2 (K), or goat antibody to the major glycoprotein of Molony Leukemia Virus, to palmitic acid. These fatty acid modified IgGs were incorporated into liposomes, and the binding of these liposomes to cells expressing the proper antigens characterized. Other in vitro efforts to specific binding of liposomes coated with specific immunoglobins have been performed (Sharkey et.al., Fed. Proc., 38, 1089, 1979). In still other coupling studies, Rahman et. al. found that tissue uptake of liposomes could be altered by attachment of glycolipids to the liposomes (*J. Cell Biol.*, 83, p. 268a, 1979).

In accordance with a primary use for liposomes, the entrapment of antineoplastic agents inside liposomal bilayers has resulted in more efficacious therapy as compared to direct administration of the drug. (Forssen et.al., *Cancer Res.*, 43, p. 546, 1983; and Gabizon et.al., *Cancer Res.*, 42, p. 4734, 1982). A major problem with the encapsulation of antineoplastic drugs as well as other agents is that many of these drugs have been found to be rapidly released from liposomes after encapsulation. This is an undesirable effect, in view of the fact that toxicity of many of the antineoplastic agents can be significantly reduced through liposome encapsulation as compared to direct administration. See, for example, Forssen et.al. Cancer Res. 43, 546 (1983) and Rahman et.al. *Cancer Res*, 42, 1817 (1982). In addition, certain pharmacological agents which are favorably delivered in sustained released fashion are not accommodated by standard liposomal delivery systems; many liposomal compositions release the agent too rapidly to provide sustained release delivery.

One answer to the above-described problem is the use of preformed, stable liposomes which maintain the stability and sustained release characteristics of the liposomal system. Liposomal compositions comprising protein-coupled liposomes have produced storage stable liposomes which may be stored stably for an indefinite period, as described in U.S. Patent No. 4,885,172, issued Dec. 5, 1989 entitled "Novel Composition for Targeting, Storing and Loading of Liposomes". These liposomes, which include streptavidin and immunoglobulin coupled to liposomes, may be stored in a dehydrated state, with loading of the liposomes on an "as needed" basis. These protein-coupled liposomes have been loaded with ionizable antineoplastic agents wherein a transmembrane potential is created across the walls of the liposomes and the antineoplastic agent is loaded into the liposomes by means of the transmembrane potential. See, for example, U.S. patent application Ser. No. 749,161, Bally et.al. entitled "Encapsulation of Antineoplastic Agents in Liposomes," filed June 26, 1985, relevant portions of which are incorporated herein by reference.

As explained above, protein-liposome conjugates have many potential applications, ranging from diagnostic systems to the targeting of disease states in vivo. As indicated elsewhere [Loughery, et al., *Biochim. Biophys Acta.*, 901, 157 (1987], the coupling of streptavidin to liposomes results in a flexible basic system which subsequently allows the straightforward conjugation of a wide variety of proteins. However, liposome-protein conjugates tend to aggregate during the conjugation process, particularly at high protein to lipid ratios. For example, it has been found that increased amounts of protein [F(ab) fragments]conjugated to liposomes resulted in an increase in the polydispersity of vesicle populations [See Bredehorst R., et al., *Biochemistry*, 25, 5693 (1986)]. It has also been observed that conditions which increase the coupling efficiency of protein to liposomes, such as increasing the lipid concentration and the ratio of protein to lipid in the coupling incubation step, increase the extent of vesicle-aggregation as observed by negative staining [See Heath, et al., *Biochim. Biophys. Acta*, 599, 42 (1980)].

Aggregation of protein-liposome conjugates during protein coupling, unfortunately, is a characteristic which impairs the general applicability of this system. This aggregation phenomenon is associated with an increased size of liposomes. It has been observed that the rate of clearance of liposomes from the circulation is dependent on the size of the preparation; the larger the liposome, the faster it is removed from the circulation [See Hunt, A.C., *Biochim. Biophys. Acta,* 719, 450 (1982) and Sota, et al., *Chem. Pharm. Bull.*, 34, 4244 (1986)]. Because of the tendency of protein liposome conjugates to aggregate, the size of such preparations has tended to be large and thus, circulation times have been somewhat disadvantageous. The clearance of protein-liposome conjugates from the blood has tended to be greater than non-conjugated liposomes of the same size. In addition, aggregated protein-liposome conjugates tend to be poorly taken up by cells via an endocytosis process which may diminish the amount of agent which enters the cells. In diagnostics, the aggregated conjugates tend to precipitate out of solution resulting in potential inaccuracies in diagnosis.

There is, therefore, a need in the art for a general method for producing protein-liposome conjugates of defined size distribution which may be utilized for general targeting applications. Such sized protein-liposome conjugates would be expected to show the favorable characteristics of protein-liposome formulations for targeting active agent delivery, including high cell uptake, or for use in diagnostics, without exhibiting substantial precipitation of aggregated protein-liposome conjugates.

It is an object of the present invention to provide a general method of attaching protein molecules to liposomes to achieve well-characterized sized protein-liposome conjugate systems for general targeting applications.

It is an additional object of the present invention to present a technique for the generation of sized protein-liposome conjugates which should allow ease of conjugating protein to liposome without affecting the binding activity of the protein to which the liposome is conjugated.

It is a further object of the present invention to provide a general method for the generation of protein-liposome conjugates of defined size distribution which can accommodate varying amounts of protein.

It is still a further object of the present invention to provide stable protein-liposome conjugates which are produced by the method of the present invention.

It is still an additional object of the present invention to provide a general method to allow for easy manipulation of the physical size of protein-coupled liposomes without affecting the binding activity of the protein.

It is yet another object of the present invention to enhance the efficiency of the production of sized protein liposome conjugates by providing an efficient coupling technique in combination with stable cross-linkages to increase the in vitro capabilities and stability of the conjugates to more efficiently deliver encapsulated materials to cells.

It is a further object of the present invention to provide sized protein-liposome conjugates which can be stored stably for long periods of time.

It is still another object of the present invention to provide sized protein-liposome conjugates which may be loaded with a bioactive agent using a transmembrane ion potential.

SUMMARY OF THE INVENTION

In the method of the present invention, liposomes are linked to a protein, for example streptavidin or an immunoglobulin, among other proteins, via a covalent or noncovalent linkage to produce an aggregated protein-liposome conjugate. This aggregated, conjugated liposomal preparation is then extruded through a filter having a pore size ranging from about 30 nm to about 100 n to produce sized protein-liposome conjugates. It has been found that the extrusion of the protein-liposome conjugate after coupling reverses the aggregation that is produced when proteins are coupled to liposomes to produce stable, non-aggregated protein-liposome conjugates of consistent size which do not readily re-aggregate. It is a surprising result that the extrusion process occurs without filtering out the aggregated protein-liposome conjugates.

The method of the present invention allows easy manipulation of the physical size of protein-liposome conjugates and may avoid affecting the binding activity of the protein. Stable protein-liposome conjugates of defined size distribution can readily be prepared with various amounts of protein attached to the liposomes by this technique. The enhanced blood circulation times of extruded conjugates and the retention of binding capacity in the experiments performed indicate that extruded preparations of protein-coupled liposomes should be capable of binding to protein binding sites in vivo.

The present invention also relates to protein-liposome conjugates. Although the weight percentages of the various components of this aspect of the present invention may vary greatly, in general, the protein-liposome conjugates of the present invention comprise:

1. a liposome vesicle comprising:
   a. at least about 90 mole percent of a liposome producing lipid; and
   b. at least about 0.1 mole percent of a functionalized lipid; and
   c. a protein linked to said functionalized lipid in an amount equal to about 10 to about 100 protein molecules per liposome vesicle.

Liposomes of the present invention may be loaded with a bioactive agent as well as pharmaceutical agents, for example local anaesthetics, brochodilators, beta-adrenergic blockers, antihypertensive agents, anti-depressants, anti-convulsants, anti-histamines, anti-malarial agents and analgesics among a number of other pharmaceutical agents. To load an active agent into the liposomes of the present invention, the liposomes are preferably prepared in such a way as to create a transmembrane potential across their lamellae in response to a concentration gradient. This concentration gradient may be created by either a $Na+/K+$ potential or a pH gradient ($H+$). The difference in internal versus external potential is the mechanism which drives the loading of the liposomes with ionizable bioactive agents; delayed loading of preformed liposomes will occur in response to the transmembrane potential.

The protein-liposome conjugates of the present invention may be dehydrated in the presence of one or more protecting sugars, stored in their dehydrated condition, and subsequently rehydrated with retention of the ion gradient and associated ability to accumulate the bioactive agent. In addition, the protein-liposome conjugates of the present invention may be used in diagnostic assays.

BRIEF DESCRIPTION OF THE DRAWINGS

FIG. 2 is a freeze fracture of streptavidin-liposome preparations. Streptavidin-liposome samples were quenched with N-ethylmaleimide at 0.2 (A), 2 (B), 4 (C) and 18 (D) hours prepared as described for Example 8 and FIG. I, above and examined by freeze fracture.

FIG. 5 is a freeze fracture of streptavidin liposomes before and after extrusion as described in Example 9. Streptavidin was coupled to liposomes at a final lipid concentration of 20 mM for 8 hours as described in FIG. 1 and Example 9. The sample was diluted to 5 umoles/ml prior to extrusion Noncovalent attachment of streptavidin to liposomes containing biotin-PE (0.25%) was performed as described in Example 1 at a final lipid concentration of 5 mM. Samples were examined by freeze fracture before and after extrusion through 100 nm polycarbonate filters. Indicated in the FIG. are Streptavidinliposomes containing MPB-PE before (A) and after (B) extrusion and Streptavidin-liposomes containing biotin-PE before (C) and after (D) extrusion.

DETAILED DESCRIPTION OF THE INVENTION

Figure 1:
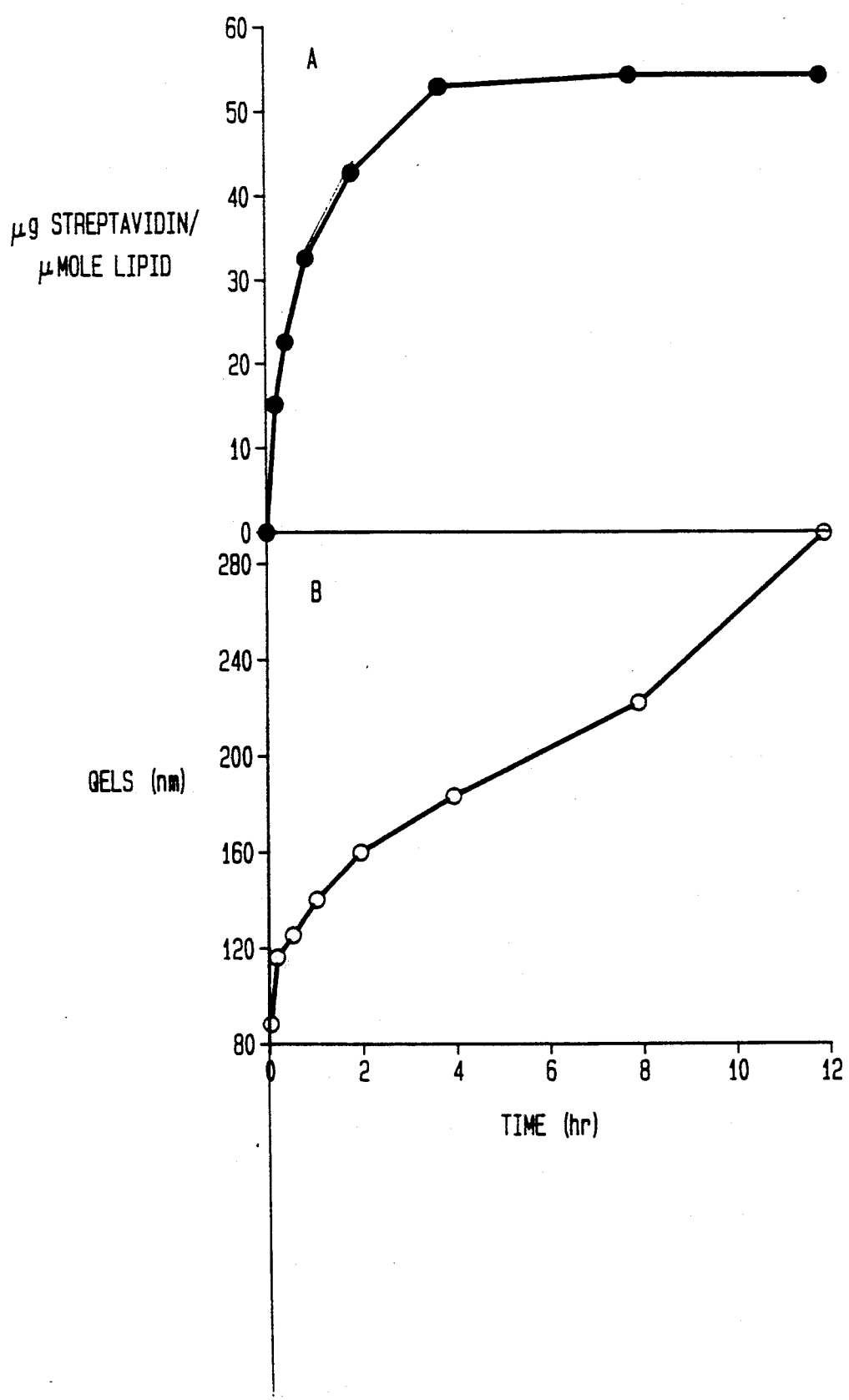
FIG. 1 is a graph showing the effect on vesicle size of coupling streptavidin to liposomes. As described in Example 8, liposomes (54% EPC, 45% CHOL, 1% MPB-PE, 5 mM final lipid concentration, 100 nm) were incubated with streptavidin (100 ug protein/umole lipid) over time at pH 7.5. At various times as indicated on the graph, the reaction was quenched by the addition of N-ethylmaleimide (500 molar ratio to protein) and free streptavidin was removed by gel filtration on sepharose CL-4B. The extent of coupled streptavidin was determined by $^3H$ biotin binding (graph A) and vesicle size was estimated by QELS (Graph B).

As described hereinabove, the present invention describes a method for producing sized protein-liposome conjugates. In the method of the present invention a liposome is first formed which comprises at least about 0.1 percent of a functionalized lipid and at least about 90 mole percent of a liposome producing lipid. Such a liposome is termed a reactive liposome. A reactive liposome is a liposome containing a functionalized lipid which will covalently or non-covalently bind to protein. After the reactive liposome is formed, a protein is coupled to the liposome to produce a protein-liposome conjugate. After the protein-liposome conjugate is formed, the conjugate is then extruded through a filter having a pore size ranging from about 30 nm to about 100 nm to produce sized protein-liposome conjugates. It has been found that the use of an extrusion step after the protein-liposome conjugate is formed results in nonaggregated protein-liposome conjugates of relatively small size, which are quite stable and which exhibit favorable blood circulation times. Surprisingly, during the extrusion step, the aggregated protein-liposome conjugates are not filtered out.

Any number of prior art methods may be utilized to covalently or non-covalently bind the protein to reactive liposomes to form the protein-liposome conjugates of the present invention. In general, however, the reactive liposomes are formulated to contain at least about 0.1 mole percent of a functionalized lipid, preferably no greater than about 10 mole percent and most preferably about 0.25 to about 1 mole percent of a functionalized lipid. As used throughout the specification of the present application, a functionalized lipid is any lipid which will form a liposome in combination with other liposome producing lipids and will bind (covalently or non-covalently) to a protein. A large number of functionalized lipids are contemplated by the present invention and are generally formed by reacting any one of a number of standard lipids used to form liposomes, for example, phosphatidylethanolamine (PE), with a bifunctional agent, for example, N-succinimidyl 4-(pmaleiimidophenyl) butyrate (SMPB) and N-succinimidyl 3-(2pyridyldithiol) proprionate (SPDP), N-succinimidyl trans-4-(N-maleimidylmethyl)cyclohexane-1-carboxylate (SMCC), and Nsuccinimidyl 3-maleimidylbenzoate (SMB) among others, to produce, for example the functionalized lipids MPB-PE and PDP-PE.

Functionalized lipids useful in the present invention are formed in two ways. The first way is by reacting a lipid with a bifunctional agent containing at least two functional groups; one of which covalently binds to the lipid and the other of which may be further reacted with a protein to produce a covalently linked protein-liposome conjugate. A bifunctional agent as used throughout the specification is a chemical agent which contains at least two distinct reactive groups which function to crosslink a lipid to a protein or a cofactor. Depending upon the chemistry of the functionalized lipid employed, the bifunctional reagent may contain at least two electrophilic groups such as activated esters, at least two nucleophilic groups such as amines, hydroxyls or thiols, or alternatively, at least one electrophilic group and one nucleophilic group. Of course, one of ordinary skill in the art would choose the bifunctional reagent to maximize the production of covalent linkages between the bifunctional reagent and the lipid or protein. Where needed, blocking groups, readily available in the art, are to be used to maximize the production of covalent linkages and prevent reaction between two different bifunctional reagents.

Alternatively, a functionalized lipid may also be formed by reacting a lipid, which contains a reactive group such as an amine or a hydroxyl group, for example, PE with an intermediate, for example, N-succinimidylbiotin or p-nitrophenylbiotin to introduce onto the lipid a cofactor or other group, for example, biotin, to which certain proteins readily non-covalently bind, to form biotin-PE. Functionalized lipids to which are bound cofactors, will non-covalently bind to a biotin-requiring protein such as streptavidin or avidin to produce non-covalently bound protein-liposome conjugates of the present invention.

The functionalized lipid is mixed with other traditional liposome producing lipids to produce reactive liposomes. The functionalized lipid generally comprises at least about 0.1 mole percent, preferably no greater than 10 mole percent and most preferably between about 0.25 and about 1 mole percent of the total lipid content of the reactive liposomes. While it is recognized that the amount of functionalized lipid which may be incorporated into liposomes may be greater than 10 mole percent such an amount serves no useful function in the present invention.

In the general method of the present invention, after the liposome vesicle containing the functionalized lipid is formed, a protein is then bound to the reactive liposome through the functionalized lipid. Any protein may be bound to the liposome. However, the present invention preferably contemplates those proteins which covalently or non-covalently bind to the liposome and maintain their natural integrity so that, after binding to the reactive liposome, the protein may also bind to a target such as a receptor site, an antigenic determinant or other binding site. Proteins which ar useful in the present invention include streptavidin, antibodies, for example immunoglobulins such as IgG, IgM, IgE, monoclonal antibodies, enzymes, immunomodulators, for example interleukin-1, interleukin-2, tumor necrosis factor (TNF) and peptides for use in vaccination, among others.

Proteins useful in the present invention may be covalently linked to the functionalized lipid of the liposome or alternatively, may be non-covalently linked to the functionalized lipid through, for example, a cofactor, such as biotin. Covalent linkages between the proteins and the functionalized lipid may be formed by the reaction of cysteinyl thiol groups naturally present within the protein with the functionalized lipid, or alternatively, the protein may be modified with a bifunctional reagent, for example, SPDP, to yield modified proteins having a reactive group, for example, a thiol which will react with the functionalized lipid. Where the protein to be covalently linked to the functionalized lipid contains at least two natural cysteinyl thiol groups which are relatively exposed, i.e., sufficiently exposed to the external surface of the protein to react with the functionalized lipid of the liposome without affecting the binding of the protein to a target site, there may be no need to modify the protein with a bifunctional reagent. However, where the protein to be covalently linked to the liposome contains no cysteinyl residues or the cysteinyl residues can only be exposed by disturbing the binding of the protein with a target, it may be necessary to functionalize the protein with a bifunctional reagent. The function of the protein bifunctional reagent is to covalently bind the protein to the functionalized lipid.

Bifunctional reagents useful in this aspect of the present invention include the same bifunctional reagents which may be used to bind to the lipid to produce a functionalized lipid. In this aspect of the present invention, the bifunctional reagent contains at least one group reactive with the protein and at least one group reactive with the functionalized lipid. A large number of bifunctional reagents are useful in the present invention, as indicated hereinabove. A particularly preferred bifunctional reagent useful in this aspect of the present invention is SPDP.

In another aspect of the present invention, the protein may first be covalently linked to a cofactor, for example, biotin before producing the protein-liposome conjugate. The proteinbiotin composition may then be covalently linked to the functionalized lipid of the reactive liposome to produce a protein-liposome conjugate to which the cofactor is covalently bound. In this aspect of the invention where biotin is the cofactor employed, a protein such as streptavidin may be reacted with N-hydroxysuccinimide biotin or p-nitrophenyl biotin to produce a covalently biotinated protein for use in producing the protein-liposome conjugate.

In another aspect of the present invention, the protein-liposome conjugates containing streptavidin or other biotinbinding protein can be further coupled to proteins such as Immunoglobulin G or monoclonal antibodies which have been biotinated by coupling to biotin with, for example N-hydroxysuccinimide. Quite surprising is the observed stability of the protein-liposome conjugates which makes the proteins an attractive coupler between the liposomes and the target sites.

In the aspect of the present invention in which protein is non-covalently bound to the reactive liposome, the liposomes are first formed utilizing most preferably between about 0.1 mole percent and about 1 mole percent of a functionalized lipid, for example phosphatidylethanolamine, covalently linked to a cofactor, substrate or other molecule to which a protein will bind non-covalently. A preferred example of a cofactor to which certain proteins, for example, avidin and streptavidin will readily bind is biotin. In certain aspects of the present invention where biotin is used, biotin is introduced onto phosphatidylethanolamine to produce the functionalized lipid biotin-PE. The functionalized lipid is incorporated into a reactive liposome and a protein is non-covalently bound to the cofactor of the functionalized lipid. In certain aspects of the present invention the protein streptavidin is used to covalently bind to biotin of the functionalized lipid.

When protein is covalently or non-covalently linked to liposomes to produce protein-liposome conjugates, the liposomes tend to aggregate and increase in size. Without being bound by theory, it is believed that the aggregation phenomenon exhibited by protein-liposome conjugates may be the result of cross-linking that occurs between a protein containing more than one reactive group which links to functionalized lipids on more than one liposome, or alternatively, between a protein which non-covalently links cofactors on more than one liposome. In the case of non-covalent binding of streptavidin, the aggregation is believed to be the result of streptavidin being able to non-covalently bind to four biotin units on different liposomes. As a result of this cross-linking, the liposomes tend to aggregate or clump together, producing liposomes of greater size than the reactive liposomes to which the protein was bound. Based on the experiments performed, the amount of protein incorporated into the protein-liposome conjugate affects aggregation. As more protein is utilized the greater is the likelihood for cross-linking and aggregation and in general, the greater will be the size of the resultant protein-liposome conjugate.

The amount of protein utilized in the protein-liposome conjugate of the present invention ranges depending upon the size of the protein used, the strength of binding between the protein and a target site and the size of the liposome used. Generally, the protein is linked to the functionalized lipid in an amount equal to about 10 to about 100 protein molecules per liposome vesicle, and most preferably about 55 to about 80 protein molecules per liposome vesicle.

In the method of the present invention, it has been discovered that extruding the aggregated liposomes after attachment of the protein to the liposome reduces the size of the aggregated liposomes and produces smaller, stable, non-aggregated protein-liposome conjugates which exhibit significantly increased blood circulation times. By stable it is meant that the protein-liposome conjugates maintain the same approximate size and protein binding to a target for at least on hour and preferably at least four hours after extrusion. It is a surprising result that the protein-liposome conjugates are not filtered out during the extrusion process.

In the extrusion aspect of the present invention, aggregated protein-liposome conjugates are passed through filters having pore sizes generally ranging from about 30 nm to about 100 nm to produce protein-liposome conjugates ranging in size from about 75 to about 200 nm in diameter. Preferably, the pore size of the filters through which the protein-liposome conjugates are extruded ranges from about 50 nm to about 100 nm. The filters are generally made of polycarbonate, but the filters may be made of any durable material which does not interact with the protein-liposome conjugate and which is sufficiently strong to allow extrusion under sufficient pressure. Preferred filters include "straight through" filters because they generally can withstand the higher pressure of the preferred extrusion process of the present invention. Although less preferred, "tortuous path" filters may also be used.

Any extrusion process available in the art may be used to produce the sized protein-liposome conjugates of the present invention and the extrusion of protein-liposome conjugates of the present invention may be performed sequentially or "straight through" under high pressure. Particularly preferred extrusion processes for use in the present invention include those disclosed in Cullis, et al., PCT Application PCT/US85/01161, Publication Number WO 86/00238 entitled "Extrusion Techniques for Producing Liposomes", published Jan. 16, 1986, relevant portions of which are incorporated by reference herein.

The present invention also relates to protein-liposome conjugates that result from the coupling of the liposomes to protein followed by an extrusion process. After the protein-liposome conjugates of the present invention are extruded, they may be dehydrated and rehydrated or alternatively, stored stably at 4 C. These compositions may be loaded with a chosen bioactive agent by potential difference of ions across the bilayer membranes after formation, during the rehydration step or subsequently thereto. Preferred methods for loading bioactive agents into liposomes include those disclosed by Madden, et al., in United States Application Serial Number 352,497, filed May 15, 1989, entitled "Accumulation of Drugs Into Liposomes by a Proton Gradient", relevant portions of which are incorporated by reference herein. Alternatively, the bioactive agent may be added to the protein-liposome conjugates prior to dehydration.

The protein-liposome conjugates of the present invention may be administered to a subject, for example a mammal including humans. The composition may be delivered to such a subject parenterally in a pharmaceutically acceptable carrier or diluent such as phosphate buffered saline. The proteins bound to the liposomes aid in targeting the liposomes and their contents to a specific site in the body. When used parenterally as in the case of bioactive agents such as antineoplastic agents, the amount used will be determined by the physician, and the treatment procedure as determined by the size of the tumor or other condition.

The protein-liposome conjugates of this invention may also be used in diagnostic assays; in this case the amount of the protein-liposome conjugate used will depend on the sensitivity of the liposome-coupled antibody to the target components in the sample.

In certain preferred embodiments, the reactive liposomes used to form protein-liposome conjugates are themselves formed using the LUVET apparatus described in copending U.S. patent application entitled "Extrusion Technique for Producing Unilamellar Vesicles", Serial No. 622,690, filed June 20, 1984, relevant portions of which are incorporated herein by reference, and coupled to strepavidin using a modified technique of Leserman et.al., (*Liposome Technology, III*, 1984, CRC Press, Inc., N.Y., p. 29–40). Liposomes may be formed with a transmembrane potential i.e., a Na+/-K+or H+gradient across the bilayers, see copending U.S. patent application, Ser. No. 749,161, Bally et.al., entitled "Encapsulation of Antineoplastic Agents in Liposomes", filed June 26, 1985, relevant portions of which are incorporated herein by reference; this potential difference is effected by the ionic concentrations of the internal versus the external media of the liposome. After loading the liposomes with bioactive agent, the liposomes are then dehydrated either in the presence or absence of sugars such as trehalose, and may be stored in this state for indefinite periods of time; see copending U.S. patent application, Ser. No. 759,419, Janoff et.al., entitled "Dehydrated Liposomes," filed July 26, 1985, relevant portions of which are incorporated herein by reference.

The reactive liposomes used in the present invention can have a variety of compositions and internal contents, and can be in the form of multilamellar, unilamellar, or other types of liposomes, or more generally, lipid-containing particles, now known or later developed. For example, the lipid-containing particles can be in the form of steroidal liposomes, stable plurilamellar liposomes (SPLVs), monophasic vesicles (MPVs), or lipid matrix carriers (LMC) of the types disclosed in commonly assigned U.S. patent applications Ser. Nos. 476,496, 521,176, 91,576 and 599,691, filed Mar. 24, 1983, Aug. 8, 1983, Mar. 20, 1984, and Apr. 12, 1984, respectively, the pertinent portions of which are incorporated herein by reference. However, it is to be recognized that the liposome should comprise at least about 0.1 mole percent and preferably no greater than about 10 mole percent of a functionalized lipid as herein defined.

Lipids which can be used in the liposome formulations of the present invention include synthetic or natural phospholipids and may include phosphatidylcholine (PC), phosphatidylethanolamine (PE), phosphatidylserine (PS), phosphatidylglycerol (PG), phosphatidic acid (PA), phosphatidylinositol(PI), sphingomyelin (SPM) and cardiolipin, among others, either alone or in combination. The phospholipids useful in the present invention may also include dimyristoylphosphatidylcholine (DMPC) and dimyristoylphosphatidylglycerol (DMPG). In other embodiments, distearylphosphatidylcholine (DSPC), dipalmitoylphosphatidylcholine (DPPC), or hydrogenated soy phosphatidylcholine (HSPC) may also be used. Dimyristoylphosphatidylcholine (DMPC) and diarachidonoylphosphatidylcholine (DAPC) may similarly be used. Due to the elevated transition temperatures ($T_c$) of lipids such as DSPC ($T_c$ of about 65° C.), DPPC ($T_c$ of about 45° C.) and DAPC ($T_c$ of about 85° C.), such lipids are preferably heated to about their $T_c$ or temperatures slightly higher, e.g., up to about 5° C. higher than the $T_c$, in order to make these liposomes. In preferred embodiments, egg phosphatidylcholine is used.

In a number of embodiments of the present invention, a steroidal component may be added to the liposome. For purposes of the present invention an component including the above-described phospholipids which may be used to produce a liposome either alone or in combination with a phospholipid is termed a liposome producing lipid. In preferred embodiments of the present invention, the liposome producing lipid comprises at least 90 mole percent of the total weight of lipids of the liposome. Any of the above-mentioned phospholipids may be used in combination with at least on additional component selected from the group consisting of cholesterol, cholestanol, coprostanol or cholestane. In addition, polyethylene glycol derivatives of cholesterol (PEG-cholesterols), as well as organic acid derivatives of sterols, for example cholesterol hemisuccinate (CHS)

may also be used in combination with any of the abovementioned phospholipids. Organic acid derivatives of alpha-tocopherol hemisuccinate, (THS) may also be used. CHS- and THS-containing liposomes and their tris salt forms may generally be prepared by any method known in the art for preparing liposomes containing sterols, so long as the resultant phospholipid-sterol mixture yields stable liposomes which may be cross-linked with protein. In particular, see the procedures of Janoff, et al., U.S. Pat. No. 4,721,612, issued Jan. 26, 1988, entitled "Steroidal Liposomes", and Janoff, et al., PCT Publication No. 87/02219, published Apr. 23, 1987, entitled "Alpha Tocopherol-Based Vehicles", relevant portions of which are incorporated by reference herein. In preferred embodiments cholesterol is utilized in combination with EPC in a weight ratio of cholesterol to EPC of about 45:54.

Techniques used for producing large unilamellar liposomes (LUVs), such as, reverse-phase evaporation, infusion procedures, and detergent dilution, can be used to produce the reactive liposomes. A review of these and other methods for producing liposomes can be found in the text *Liposomes*. Marc J. Ostro, ed., Marcel Dekker, Inc., New York, 1983, Chapter 1, the pertinent portions of which are incorporated herein by reference.

Several extrusion methods may be used to produce reactive liposomes or alternatively, protein-liposome conjugates. Preferably, to produce reactive liposomes, MLVs are extruded through filters forming large unilamellar vesicles (LUVs) of sizes dependent upon the filter size utilized. In general, polycarbonate filters of 30, 50, 60 or 100 nm pores may be used to produce the sized protein-liposome conjugates of the present invention. In this method, disclosed in Cullis, et al., PCT Publication Ho. WO 86/000238, Jan. 16, 1986, relevant portions of which are incorporated by reference herein, the liposome suspension may be repeatedly passed through the extrusion device resulting in a population of liposomes of homogeneous size distribution. For example, the filtering may be performed through a straight-through membrane filter (a Nucleopore polycarbonate filter) or a tortuous path filter (e.g. a Nucleopore filter membrafil filter (mixed cellulose esters) of 0.1 um size), or by alternative size reduction techniques such as homogenization. Although the size of the reactive liposomes may vary from about 30 to above about 200 nm in diameter, preferably, the reactive liposomes are about 100 nm to about 200 nm in size. Generally, sized protein-liposome conjugates range in size between about 75 nm and about 200 nm.

As described hereinabove, a number of lipids may be used to form reactive liposomes having a gel to liquid crystalline $T_c$ above ambient temperature. In such cases, an extruder having a heating barrel or thermojacket may be employed. Such a device serves to increase the liposome suspension temperature allowing extrusion of the LUVs. The lipids which are used with the thermojacketed extruder are, for example, DSPC, DPPC, DMPC and DAPC or mixtures thereof, which may include cholesterol in certain embodiments. Liposomes containing DSPC are generally extruded at about 65° C., DPPC at about 45° C. and DAPC at about 85° C. (about 5° C. above the lipid $T_c$).

After extrusion, the reactive liposomes or protein-liposome conjugates may be loaded with bioactive agent or dehydrated for storage. However, in the case of protein-liposome conjugates, some loss of bioactive agent may result during the extrusion step. To avoid this possible result, it is preferred to load the bioactive agent after extrusion. The liposomes and protein-liposome conjugates of the present invention may be dehydrated using standard freeze-drying equipment or equivalent apparatus, and, if desired, the liposomes or protein-liposome conjugates and their surrounding medium can be frozen in liquid nitrogen before being dehydrated. Alternatively, the liposomes and protein-liposome conjugates can also be dehydrated without prior freezing, by simply being placed under reduced pressure. Dehydration with prior freezing requires the presence of one or more protective sugars in the preparation. A variety of sugars can be used, including such sugars as trehalose, maltose, sucrose, glucose, lactose, and dextran. In general, disaccharide sugars have been found to work better than monsaccharide sugars, with the disaccharide sugars trehalose and sucrose being most effective.

The one or more sugars are included as part of either the internal or external media of the liposomes or protein-liposome conjugates. Most preferably, the sugars are included in both the internal and external media so that they can interact with both the inside and outside surfaces of the liposomes' and protein-liposome conjugates' membranes. Inclusion in the internal medium is accomplished by adding the sugar or sugars to the solute which the liposomes are to encapsulate. Since in most cases this solute also forms the bathing medium for the finished liposomes, inclusion of the sugars in the solute also makes them part of the external medium. Of course, if an external medium other than the original solute is used, e.g., to create a transmembrane potential (see below), the new external medium should also include one or more of the protective sugars.

In the case of dehydration without prior freezing, if the liposomes and protein-liposome conjugates being dehydrated have multiple lipid layers and if the dehydration is carried out to an end point where there is sufficient water left in the preparation so that a substantial portion of the membranes retain their integrity upon rehydration, the use of one or more protective sugars may be omitted. It has been found preferable if the preparation contains at the end of the dehydration process at least about 2%, and most preferably between about 2% and about 5%, of the original water present in the preparation prior to dehydration.

Once the liposomes or protein-liposome conjugates have been dehydrated, they can be stored for extended periods of time until they are to be used. When the dehydrated liposomes or protein-liposome conjugates are to be used, rehydration is accomplished by simply adding an aqueous solution, e.g., distilled water, to the liposomes or protein-liposome conjugates and allowing them to rehydrate.

As discussed hereinabove, the liposomes and protein-liposome conjugate preparation of the present invention may be loaded with ionizable pharmacological agents, for example antineoplastic agents, wherein a transmembrane potential is created across the bilayers of the liposomes or protein-liposome conjugates and the antineoplastic agent is loaded into the liposomes by means of the transmembrane potential. The transmembrane potential is generated by creating a concentration gradient for one or more charged species (e.g., $Na+$, $K+$ and/or $H+$) across the liposome membranes. The concentration gradient is created by producing liposomes and protein-liposome conjugates having different internal and external media, i.e., internal and external media having different concentrations of one or more charged species.

Specifically, reactive liposomes used to produce the protein-liposome conjugates of the present invention are prepared which encapsulate a first medium having a first concentration of the one or more charged species. For a typical liposome preparation technique (see discussion above), this first medium will surround the liposomes as they are formed, and thus the liposomes, original external medium will have the same composition as the first medium. To create the concentration gradient, the original external medium is replaced by a new external medium having a different concentration of the one or more charged species. The replacement of the external medium can be accomplished by various techniques, such as, by passing the liposome preparation through a gel filtration column, e.g., a Sephadex column, which has been equilibrated with the new medium, or by centrifugation, dialysis, or related techniques.

In accordance with the invention, it has been found that this transmembrane potential can be used to load ionizable antineoplastic agents into the liposomes or alternatively, into the sized protein-liposome conjugates. Specifically, once liposomes having a concentration gradient and thus a transmembrane potential of the appropriate orientation have been prepared, the process of loading pharmaceutical agents into the liposomes reduces to the very simple step of adding the agent to the external medium. Once added, the transmembrane potential will automatically load the agent into the liposomes.

The transmembrane potential loading method can be used with essentially any pharmacological agent, including antineoplastic agents, which can exist in a charged state when dissolved in an appropriate aqueous medium (e.g., organic compounds which include an amino group which can be protonated). Preferably, the agent should be relatively lipophilic so that it will partition into the liposome membranes. Examples of some of the pharmacological agents which can be loaded into liposomes by this method include antineoplastic agents, for example, doxorubicin, mitomycin, bleomycin, daunorubicin, streptozocin, vinblastine, vincristine, mechlorethamine hydrochloride, melphalan, cyclophosphamide, triethylenethiophosphoramide, carmustine, lomustine, semustine, fluorouracil, hydroxyurea, thioguanine, cytarabine, floxuridine, decarbazine, cisplatin and procarbazine; local anaesthetics, for example, lidocaine, dibucaine and chlorpromazine; bronchodilators, for example, metaproterenol, terbutaline and isoproterenol; beta-adrenergic blockers, for example propanolol, timolol and labetolol; antihypertensive agents, for example clonidine and hydralazine; anti-depressants, for example, imipramine, amitryptyline and doxepim; anticonvulsants, for example, phenytoin; anti-emetics, for example, procainamide and prochlorperazine; antihistamines, for example, diphenhydramine, chlorpheniramine and promethazine; anti-arrhythmic agents, for example, quinidine and disopyramide; anti-malarial agents, for example, chloroquine, quinacrine and quinine; and analgesics, among a number of additional pharmaceutical agents.

In addition to loading a single pharmacological agent, the method can be used to load multiple pharmacological agents, either simultaneously or sequentially. Also, the proteinliposome conjugates into which the ionizable antineoplastic agents are loaded can themselves be pre-loaded with other antineoplastic agents or other drugs using conventional encapsulation techniques (e.g., by incorporating the drug in the buffer from which the liposomes are made).

It has been found that the rate of release of a pharmacological agent can be markedly reduced by creating a transmembrane potential across the protein-liposome conjugate membranes which is oriented to retain the agent within the conjugate. That is, for an agent which is positively charged when ionized, a transmembrane potential is created across the protein-liposome conjugate membranes which has an inside potential which is negative relative to the outside potential, while for an agent which is negatively charged, the opposite orientation is used.

As with the transmembrane loading aspects of the invention, the transmembrane potentials used to reduce the rate of drug release are created by adjusting the concentrations on the inside and outside of the liposomes or protein-liposome conjugates of a charged species such as Na+, K+ and/or H+. Indeed, if the liposomes or protein-liposome conjugates have been loaded by means of a transmembrane potential produced by such a concentration gradient, simply keeping the liposomes or proteinliposome conjugates in an external medium which will maintain the original concentration gradient will produce the desired reduction in the rate of release. Alternatively, if a transmembrane potential has not already been created across the liposome or protein-liposome conjugates membranes, e.g., if the liposomes or protein-liposome conjugates have been loaded using a conventional technique, the desired transmembrane potential can be readily created by changing the composition of the external medium using the exchange techniques described above.

In the method aspect of the invention relating to dehydration of the protein-liposome conjugates, two basic approaches are provided. In the first approach, the conjugates can be loaded with bioactive agents (e.g., using conventional techniques or the transmembrane potential loading technique described above), dehydrated for purposes of storage, shipping, and the like, and then rehydrated at the time of use. Alternatively, pre-formed liposome conjugates can be dehydrated for storage, etc., and then at or near the time of use, rehydrated and loaded with an ionizable bioactive agent using the transmembrane potential loading technique described above.

When the dehydrated protein-liposome conjugates are to be used, rehydration is accomplished by simply adding an aqueous solution, e.g., distilled water or an appropriate buffer, to the protein-liposome conjugates and allowing them to rehydrate. The conjugates may be resuspended into the aqueous solution by gentle swirling of the solution. The rehydration can be performed at room temperature or at other temperatures appropriate to the composition of the liposomes and their internal contents.

If the bioactive agent which is to be administered is incorporated into the protein-liposome conjugates prior to dehydration, and no further composition changes are desired, the rehydrated conjugates can be used directly in therapy following known procedures for administering liposome encapsulated drugs.

Alternatively, using the transmembrane potential procedures described above, ionizable bioactive agents can be incorporated into the rehydrated protein-liposome conjugates just prior to administration. In connection with this approach, the concentration gradient used to generate the transmembrane potential can be created either before dehydration or after rehydration using the external medium exchange techniques described above.

Protein-liposome conjugates having the same internal and external media, i.e., no transmembrane potential, can be prepared, dehydrated, stored, rehydrated, and then the external medium can be replaced with a new medium having a composition which will generate transmembrane potentials, and the transmembrane potentials used to load ionizable antineoplastic agents into the liposomes. Alternatively, protein-liposome conjugates having internal and external media which will produce transmembrane potentials can be prepared, dehydrated, stored, rehydrated, and then loaded using the transmembrane potentials.

Protein-liposome conjugates of the present invention may be administered to a subject such as a mammal, including humans. For administration to humans in the treatment of afflictions, the prescribing physician will ultimately determine the appropriate dose for a given human subject, and this can be expected to vary according to the age, weight, and response of the individual as well as the nature and severity of the patient's symptoms.

The mode of administration may determine the sites in the organism to which the compound will be delivered. For instance, delivery to specific site of infection may be most easily accomplished by topical application (if the infection is external, e.g., on areas such as the eyes, skin, in the ears or on afflictions such as wound or burns) or by absorption through epithelial or mucocutaneous linings (e.g., nasal, oral, vaginal, rectal, gastrointestinal, mucosa, etc.). Such topical application may be in the form of creams or ointments. The protein-liposome conjugate containing bioactive agent may be administered alone but will generally be administered in admixture with a pharmaceutical carrier selected with regard to the intended route of administration and standard pharmaceutical practice. The protein-liposome conjugates of the present invention may be injected parenterally, for example, intravenously, intramuscularly, or subcutaneously. For parenteral administration, they are best used in the form of a sterile aqueous solution which may contain other solutes, for example, sufficient salts, glucose or dextrose to make the solution isotonic.

For the oral mode of administration, protein-liposome conjugate compositions of the present invention can be used in the form of tablets, capsules, lozenges, troches, powders, syrups, elixirs, aqueous solutions and suspension, and the like. In the case of tablets, carriers which can be used include lactose, sodium citrate, and salts of phosphoric acid. Various disintegrants such as starch, and lubricating agents, for example, starch may be used. For oral administration in capsule form, useful diluents are lactose and high molecular weight polyethylene glycols. When aqueous suspensions are required for oral use, certain sweetening and/or flavoring agents can be added.

The protein-liposome conjugates of the present invention may also be used in diagnostic assays; in this case the amount of the composition used will depend on the sensitivity of the liposome-coupled antibody to the target components in the sample.

The following examples are provided for purposes of illustration only and are not to be viewed as a limitation of the scope of the invention.

EXAMPLES

MATERIALS AND METHODS

Egg phosphatidylcholine (EPC), and dipalmitoyl phosphatidylethanolamine (DPPE) were obtained from Avanti Polar Lipids USA. Biotin-phosphatidylethanolamine (biotin-PE), N-succinimidyl 3-(2-pyridyldithio) propionate (SPDP), N-succinimidyl 4-(p-maleiimidophenyl) butyrate (SMPB) were obtained from Molecular Probes, Oregon, USA. Streptavidin, FITC-cellite, N-ethylmaleimide, dithiothreitol, cholesterol, B-mercaptoethanol, N-(2-hydroxyethyl) piperazine-N'-3-propanesulphonic acid (EPPS), 2-(N-Morpholino) ethanesulphonic acid (MES), N-2-Hydroxyethylpiperazine-N'-2-ethanesulphonic acid (HEPES) and sephadex G-50 were obtained from Sigma, USA. Anti-human erythrocyte IgG was obtained from Cappel, Inc. USA and Sepharose CL-4B from Pharmacia, Canada. $^{14}C$ cholesterol and $^3H$ cholesterol-hexadecyl-ether were obtained from New England Nuclear, Canada. $^3H$ and $^{14}C$ biotin were obtained from Amersham, Canada. Mice, averaging 21 g. in weight, were obtained from Jackson Laboratories, California, U.S.A.

EXAMPLE 1

Synthesis of N-(4-(p-Maleimidophenyl)butyryl)dioalmitoylphosphatidyl-ethanolamine (MPB-DPPE)

MPB-DPPE was synthesized by a modification of the method of Martin, et al., J. Biol. Chem., 257, 286–288, (1982). Briefly, synthesis of intact MPB-DPPE was carried out in the presence of one equivalent of triethylamine in chloroform, at a molar ratio of 1.5 SMPB:DPPE. After 3 hours, the reaction mixture was evaporated to dryness under nitrogen. Excess unreacted SMPB and major by-products were removed by preparative thin layer chromography (TLC, silica gel developed with 50% acetone in chloroform). The upper portion of the lipid band was extracted from silica with about 20 to 30% methanol in chloroform (V:V) resulting in the isolation of pure intact MPB-DPPE as characterized by $^1H$ NMR.

EXAMPLE 2

Preparation of Liposomes

Large unilamellar liposomes were prepared as described by Hope, et al. Biochim. Biophys. Acta., 812, 55 (1985). Briefly, aliquots of lipid mixtures in chloroform were deposited in a tube and dried to a lipid film under a stream of nitrogen followed by high vacuum for 2 hours. Lipid was then hydrated in 25 mM MES, 25 mM HEPES, 150 mM NaCl pH 6.5 and extruded through two stacked 100 nm or 50 nm filters 10 times. Prior to coupling experiments, samples were titrated to pH 7.5 with NaOH. Lipid was estimated either by the colorimetric method of Fiske, C. and SubbaRow, Y., J. Biol. Chem.. 66, 375 (1925) or by incorporating trace amounts of $^{14}C$ cholesterol or $^3H$ cholesterol-hexadecyl ether in the lipid mixture. The samples were assayed by scintillation counting in a Packard Tri Carb liquid or a Beckmann model LS 3801 scintillation analyzer.

EXAMPLE 3

Preparation of Proteins for Coupling

Streptavidin (10 mg/ml in 25 mM HEPES, 150 mM NaCl, pH 7.5, HBS) was modified with the amine reactive reagent, SPDP according the procedure of Carlsson, et al., Biochem. J. 173, 723 (1978). Briefly, SPDP (25 mM in methanol) was incubated at a 10 molar ration to streptavidin at room temperature for 30 minutes. To estimate the extent of modification, a portion of the reaction mixture was passed down sephadex G-50 equilibrated with HBS to remove unreacted SPDP. The extent of modification of streptavidin was determined by estimating the protein concentration at 280 nm [Extinction coefficient at 280 nm ($E_{280}$:2770)] prior to the addition of dithiothreitol (DTT) and the 2thiopyridone concentration at 343 nm ($E_{343}$:7550) 10 minutes after the addition of DTT (25 mM). The remainder of the reaction mixture was reduced with DTT (25 mM, 10 minutes) and the thiolated product was isolated by gel exclusion on sephadex G-50 equilibrated with 25 mM MES, 25 mM HEPES, 150 mM NaCl, pH 7.5. The product was immediately used in coupling experiments.

In the case of IgG (20 mg/ml in HBS), following the modification of the protein with SPDP, the protein was fluorescently labelled with FITC-cellite (50% weight of IgG in 150 mM NaCl, 0.2 M NaHC03, pH 8.8, 20 minutes). Prior to the treatment of the protein with DTT, the sample was separated from unreacted reagents on sephadex G-50 equilibrated with an acetate buffer (100 mM NaCl, 100 mM Na acetate, pH 5.0), to protect against the reduction of the intrinsic disulfides of the molecule. The sample was concentrated to 5 mg/ml by dehydration with aquacide prior to the coupling experiments. The extent of modification of streptavidin was 5-6 SPDP molecules per protein while the modification of the antibody preparation resulted in 2-3 molecules of SPDP per protein.

EXAMPLE 4

Covalent Coupling of Proteins to Liposomes

The coupling of proteins to liposomes was performed by incubating the reduced PDP-modified protein with liposomes (54% EPC, 45% cholesterol, 1% MPB-PE, sized through filters of 50 or 100 nm pore size), at a ratio of 100 ug protein/umole lipid (5 mM-30 mM final lipid concentration) at pH 7.5. The reaction was quenched at various times by the addition of N-ethylmaleimide (500 molar ratio to protein, in methanol). For in vivo experiments, samples were further quenched with B-mercaptoethanol (10 molar ratio with respect to N-ethylmaleimide) after 2 hour incubation of the reaction mixture with N-ethylmaleimide. Uncoupled protein was removed by gel filtration on sepharose CL4B equilibrated with HBS. The extent of coupling of streptavidine to liposomes was measured by the binding of $^3H$ or $^{14}C$ biotin to streptavidin. Briefly, streptavidin-liposomes (0.25 umoles lipid in 0.5 ml) were incubated with 3H or $^{14}C$ biotin (3.85 nmoles in 25 ul, 15.4 nmoles/uCi) for 10 minutes and unbound biotin was removed by gel filtration on sepharose CL-4B equilibrated with HBS. The extent of binding of biotin to a streptavidin standard (100 ug) after gel exclusion on sephadex G50 was used as a reference for the calculation of coupling ratios. For the determination of the extent of antibody (IgG) coupled to liposomes, samples (200 ul) were dissolved in ethanol (1.8 ml) and the liposomes associated fluorescence was correlated to a known quantity of fluorescein labelled antibody. Fluorescence was monitored at 520 nm using a SLC-500C spectrofluorometer with an extinction wavelength of 495 nm.

EXAMPLE 5

Preparation of Non-covalently Attached Streptavidin

Prior to the non-covalent attachment of streptavidin to liposomes, streptavidin was fluorescently labelled with FITCcellite as described above for IgG. Streptavidin (4.1 mg) was incubated for 10 minutes with liposomes (54.75% EPC, 45% cholesterol, 0.25% biotin-PE) at a 10 molar excess to biotin-PE in 20 mM Hepes-buffered saline (pH 8) for about 30 minutes. See Loughery, et al., Biochem. Biophys. Acta., 901, 157 (1987). At various times, aliquots were fractionated on Sepharose CL-4B columns (5 ml) to separate liposomally bound streptavidin from free streptavidin. The extent of coupled streptavidin was determined after gel filtration on sepharose CL-4B as described for IgG (Example 4, above).

EXAMPLE 6

Preparation and Characterisation of Extruded Protein-Liposome Samples

Protein-liposome conjugates (5 mM or 20 mM final lipid concentration) were extruded 10 times through two stacked millipore filters (50 or 100 nm). Lipid recovery was estimated by scintillation counting of an aliquot of the extruded sample. The size of the protein-coupled vesicles before and after extrusion was estimated by freeze fracture techniques and by quasi-elastic light scattering (QELS) using a Nicomp Model 270 submicro particle size operating at 632.8 nm and 5 mW.

EXAMPLE 7

In Vivo Studies of Liposome Preparations

For in vivo studies, streptavidin-liposome conjugates were prepared at a final lipid concentration of 30 mM and an incubation period of 15 minutes, as described in Examples 1 through 6. Liposomal lipid was quantified employing the nonmetabolizable, non-exchangeable lipid marker $^3H$ cholesterol-hexadecyl-ether by the method described in Huang, L., in "Liposomes", Ed. Mark J. Ostro, pp. 87-124, by Marcel Deker, New York, 1983 and Stein, et al., FEBS Lett., 11, 104 (1980), specific activity: 0.23 uCi/mg total lipid. For scintillation counting, 50-100 ul plasma was added to 5 ml PicoOFluor 40 (Packard, Canada) scintillation cocktail and samples were counted in a Beckman model LS 3801 scintillation counter. Unbound streptavidin was removed by gel exclusion on sepharose CL-4B. A portion of the sample was extruded 10 times through two stacked 50 or !00 nm filters immediately prior to injection. As controls, liposomes containing MPB-PE (54% EPC, 45% cholesterol, 1% MPB-PE) were prepared at pH 6.5 as described hereinabove. An aliquot of the lipid sample was titrated to pH 7.5 with NaOH, quenched with B-mercaptoethanol (10 molar excess to MPB-PE) and free B-mercaptoethanol was removed by gel filtration on sephadex G-50 equilibrated with HBS. Unquenched MPB-PE liposomes were exchanged on sephadex G-50 equilibrated with HBS prior to in vivo experiments. Liposomes containing 55% EPC and 45% cholesterol were prepared in HBS.

For in vivo plasma lipid level determinations, mice (4-8 per time point) were injected with samples via the tail vein at a dose of 100 mg total lipid/kg. Blood was collected in EDTA treated microcontainers (Bectin Dickinson, Franklin Lakes, New Jersey) and plasma was prepared by centrifuging (200×g) whole blood for 10 minutes in a clinical centrifuge. Total plasma volume per animal was taken to be 4.55% of mean body weight. Control blood samples containing known amounts of liposomes showed that only a minor fraction of the liposomal lipid was associated with the pelleted blood cells. The recovery of liposomes was similar if determined from whole blood or from plasma. The levels of streptavidin associated with liposomes in vivo was determined by the binding of $^{14}C$ biotin to a plasma sample isolated 1 and 4 hours post injection.

EXAMPLE 8

Characterization of Protein Conjugation on Vesicle Size

Liposomes (54%EPC, 45% CHOL, 1% MPB-PE, 5 mM final lipid concentration, 100 nm) were incubated with streptavidin (100 ug protein/umole lipid) over time at pH 7.5 as described hereinabove. At various times ranging from 5 minutes to 12 hours, as depicted in FIG. 1, the reaction was quenched by addition of N-ethylmaleimide (500 molar ratio to protein) and free streptavidin was removed by gel filtration on sepharose CL4B. The extent of coupled streptavidin was determined by $^3H$ binding (indicated in graph A of FIG. 1) and vesicle size was estimated by QELS (indicated in graph B of FIG. 1). As shown in FIG. 1, an increase in the amount of protein bound to liposomes results in a significant increase in vesicle size as recorded by QELS. The initial rapid coupling of strepavidin to vesicles correlates with a rapid increase in the size distribution of the preparation. In order to confirm this result, a freeze fracture technique for examining the morphology of the larger systems, was used to measure aliquots of the same coupling system. The results presented in FIG. 2, clearly show that the increase in size as measured by QELS is related to vesicle aggregation. However, after extended periods of incubation, a significant number of large vesicles (>200 nm) are observed, presumably due to fusion events following aggregation.

EXAMPLE 9

Effect of Extrusion on Aggregation of Liposome Conjugates

Figure 3:
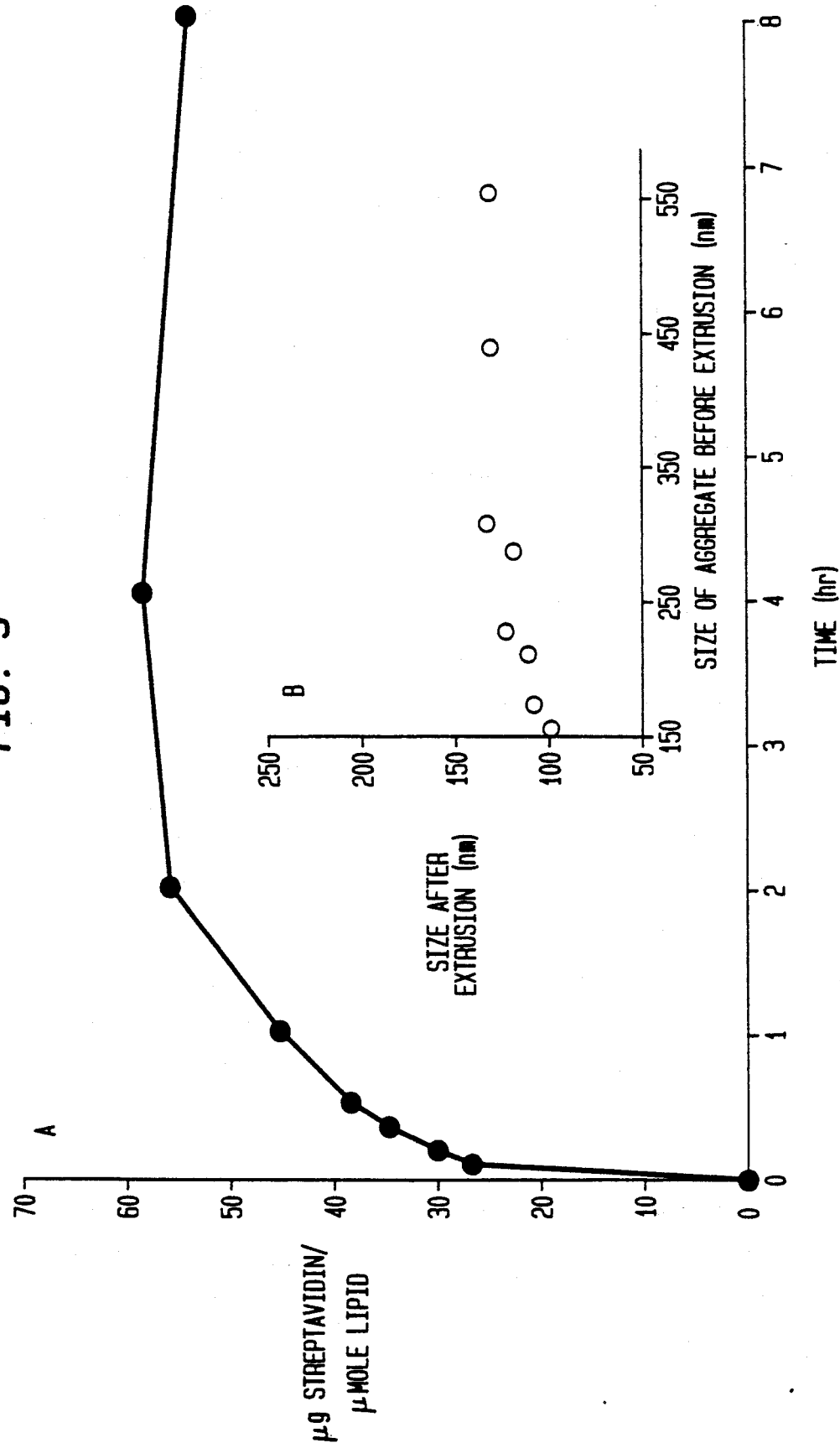
FIG. 3 is a graph representing the extrusion of streptavidin-liposome conjugates as described in Example 9. Streptavidin was coupled to liposomes (100 nm) containing 1% MPBPE at a final lipid concentration of 20 mM. At various times, aliquots of the reaction mixtures were quenched with Nethylmaleimide and diluted to 5 mM lipid concentration before extrusion through 100 nm polycarbonate filters. The extent of coupled streptavidin (A) was estimated by $^3H$ biotin binding to streptavidin liposomes after gel exclusion of lipid samples on sepharose CL-4B. The size of streptavidine-liposome conjugates was estimated by QELS before and after extrusion (B).
Figure 4:
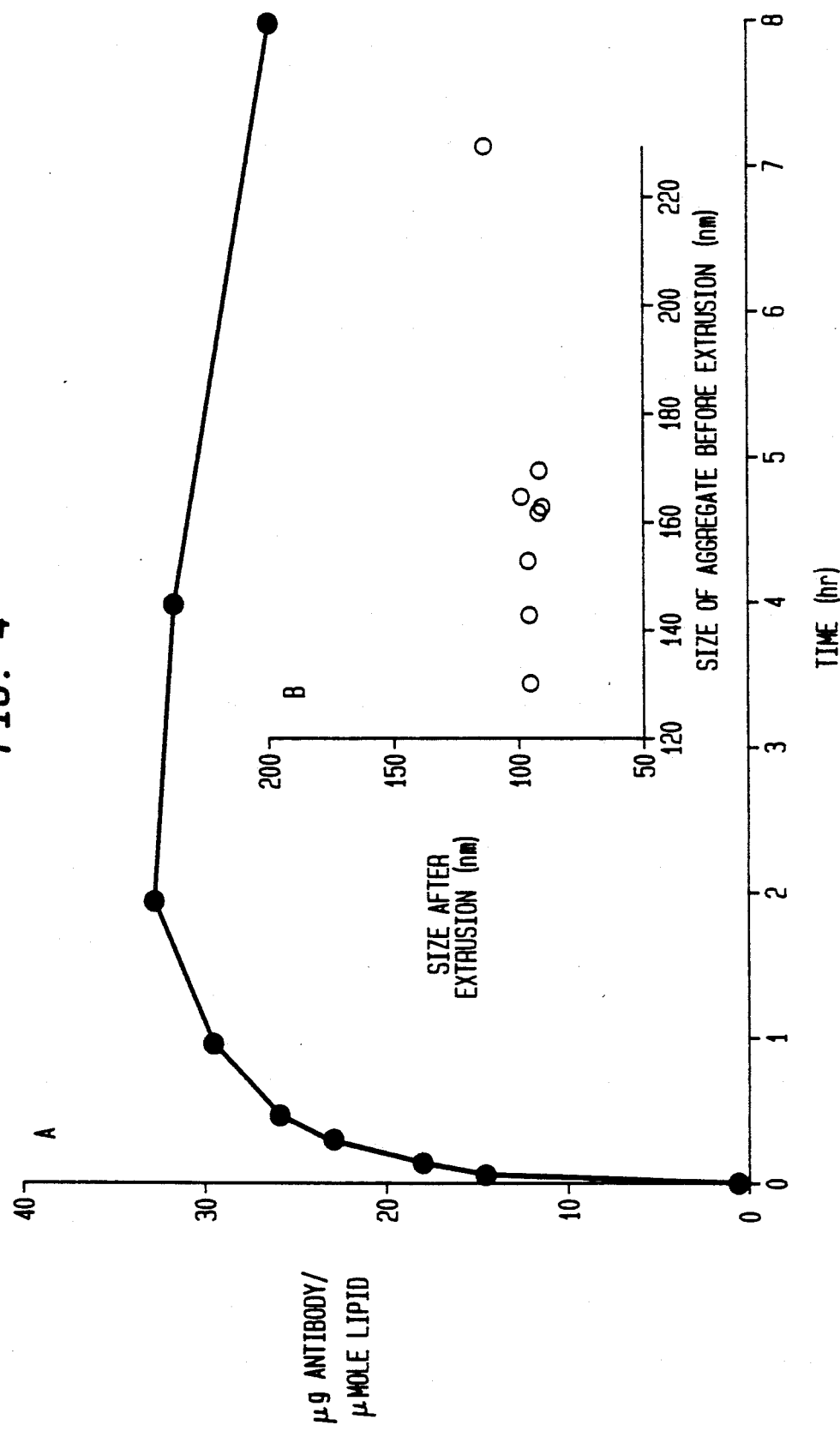
FIG. 4 is a graph representing the extrusion of antibody liposome conjugates as described in Example 9. Fluorescein labelled antibody was coupled to liposomes (100 nm) containing 1% MPB-PE at a final lipid concentration of 20 mM. At various times aliquots of the reaction mixtures were quenched with Nethylmaleimide and diluted to 5 mM lipid concentration before extrusion through 100 nm polycarbonate filters. The extent of coupled antibody (A) was determined by estimating the levels of liposomally associated fluorescence after exchange of lipid samples on sepharose CL-4B. The size of the antibody liposome was estimated by QELS before and after extrusion (b).

In an attempt to achieve small, homogeneously sized protein-liposome conjugates, the effects of extruding aggregated, conjugated vesicles through filters with 100 nm pore size were examined for liposomes with attached streptavidin (FIG. 3) or antibody (FIG. 4) as prepared hereinabove. The coupling reaction mixtures were quenched with N-ethylmaleimide at various times and the size of the coupled samples prior to and after extrusion was estimated by QELS (FIGS. 3B and 4B). The extent of coupled protein was determined after extrusion of conjugated samples (FIGS. 3A and 4A). Irrespective of the amount of protein coupled to the liposomes, vesicles coupled with streptavidine or antibody were readily extruded and the resulting preparations fell within a narrow size range. For example, extrusion of liposomes with attached streptavidin (25-60 ug/umole lipid) resulted in vesicle sizes of 120-140 nm in diameter as compared to initial size distributions of 150 to more than 500 nm.

Similarly, extrusion of antibody liposome conjugates (15-35 ug protein/umole lipid) resulted in smaller vesicles of narrow size distribution (90-110 nm) compared to the size range of 130-230 nm prior to extrusion. It is important to note that the loss of lipid for both types of protein coupled vesicles during the extrusion process was minimal (85-90% lipid recovery). These results demonstrate that a highly aggregated preparation of vesicles with high levels of conjugated protein can be extruded efficiently and the resulting preparations are of similar size.

Furthermore, the extrusion of protein-liposome aggregates represents a gentle method preparing sized protein conjugated vesicles. This was illustrated by the retention of streptavidin-liposome conjugates to bind biotin after extrusion (results not shown).

The observation that liposome conjugates aggregate during protein coupling to liposomes is not unique to the covalent attachment of proteins to liposomes. Vesicle aggregation also occurs during the non-covalent attachment of streptavidin to liposomes containing biotin-PE [See Loughery, et al., Biochem. Biophys. Acta., 901, 157 (1987)]. To demonstrate the general application of the extrusion process as a means of generating sized populations of protein-liposome conjugates, the effect of extrusion of streptavidin coupled covalently to liposomes containing MPB-PE or non-covalently bound to liposomes containing biotin-PE was examined by freeze fracture (FIG. 5). Both types of streptaviding liposome conjugates were observed to be highly aggregated prior to extrusion. After extrusion, the coupled vesicles existed as monomers of dimers with the maximum aggregate observed to be a conglomerate of 4 vesicles. In the case of the non-covalent coupling procedure (FIG. 5C and 5D), significant loss of lipid occurred (50%) during the extrusion of coupled vesicles.

EXAMPLE 10

The Stability of Extruded Liposomes

Figure 6:
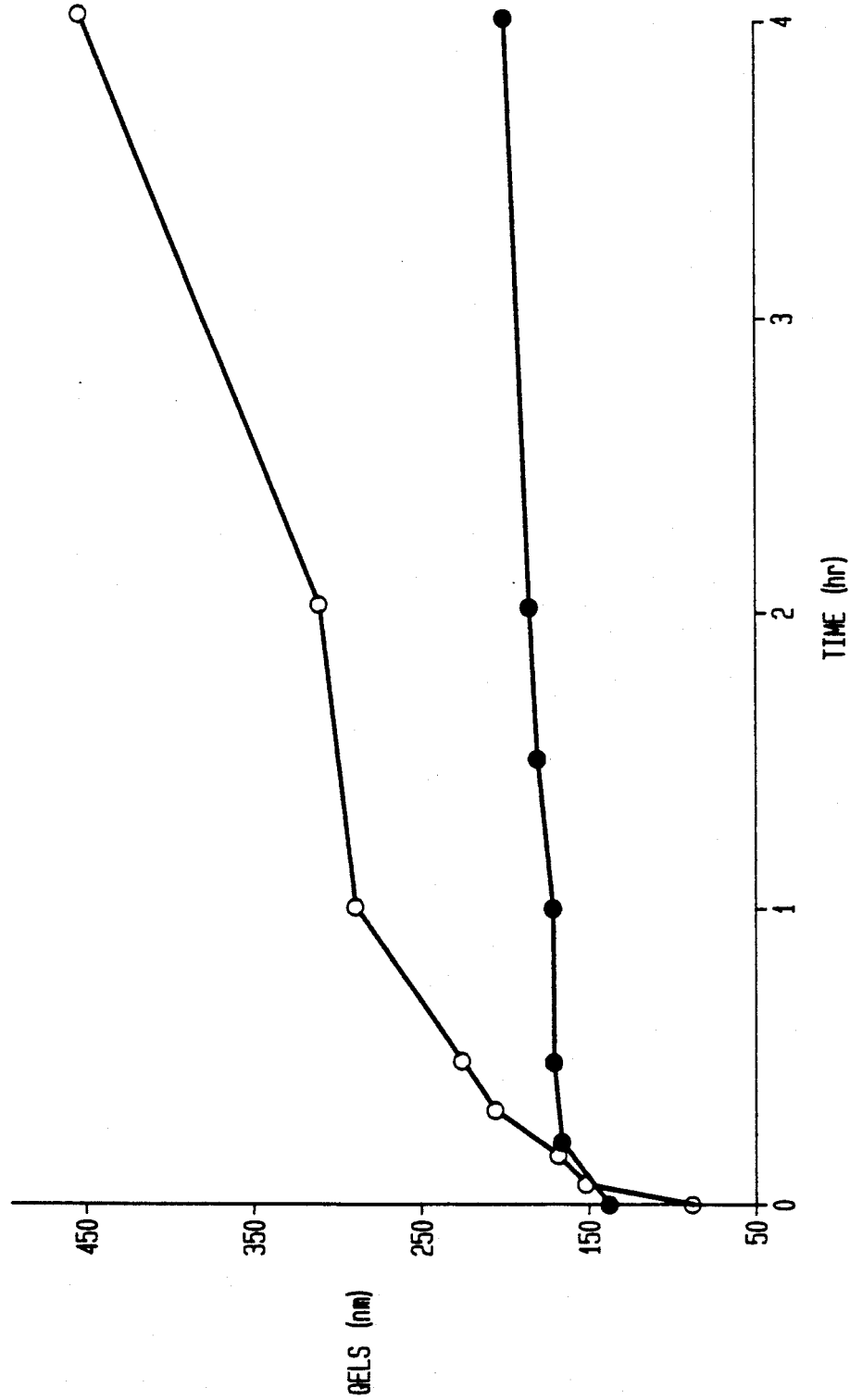
FIG. 6 represents the examination of the stability of extruded streptavidin-liposome conjugates by QELS. Streptavidinliposomes with approximately 51 ug protein/umole lipid were prepared by incubating thiolated streptavidin with liposomes containing 1% MPB-PE for 8 hours at a final lipid concentration of 20 mM. After removal of unbound streptavidin by gel filtration on sepharose CL-4B, the sample was diluted to 5 mM lipid and extruded 10 times through two stacked 100 nm polycarbonate filters. At various times as indicated the size of the extruded preparation was determined by QELS ( ). The size of streptavidin-liposome conjugates prepared as in FIG. 1 are graphed for comparison (○).

The stability of extruded samples containing covalently bound streptavidin with respect to size is represented by FIG. 6. QELS measurements indicate an initial small (30nm) rapid increase in the size of the preparation after extrusion. This was reflected by increased aggregation of the extruded vesicles as indicated by freeze fracture (results not shown). As shown in Table 1, below, the level of reaggregation observed 8 hours after extrusion of various streptavidin-liposome conjugates was minimal when compared to the aggregated state of the samples prior to extrusion. Reaggregation of liposomes was not observed when MPBPE liposomes were extruded with thiolated-streptavidin which had been quenched by prior incubation with B-mercaptoethanol (Table 1, below). This indicates that reaggregation was not due to nonspecific association of protein with liposomes. It was found that the incorporation of negatively charged lipids, for example phosphatidylserine, or the presence of low or high ionic strength buffers did not prevent reaggregation (data not shown).

The reduction of the amount of streptavidin coupled to vesicles (Table 1, below) resulted in a corresponding decrease in the extent of reaggregation 8 hours after extrusion. Varying the lipid concentrating of the extruded sample did not significantly affect the reaggregation. Streptavidin coupled to liposomes which were frozen immediately after extrusion, maintained their original size distribution on thawing. Finally, storage of the extruded samples at 4.C resulted in increased stability of liposome size.

TABLE 1

Factors Affecting the Aggregation of Extruded Streptavidin-Liposomes
QELS Size Estimates of Streptavidin Coupled to Liposomes (nm)

| ug. Streptavidin/ umol. Lipid | Lipid Conc. (mM) | Before Extrusion | After Extrusion 0 Hrs | After Extrusion 8 Hrs |
|---|---|---|---|---|
| 0[c] | 2.5 | 110 | 104 | 104 |
| 17.1[a] | 2.5 | 177 | 109 | 119 |
| 31.6[a] | 2.5 | 232 | 119 | 140 |
| 45.3[a] | 2.5 | 286 | 123 | 154 |
| 45.1[b] | 5.0 | 403 | 174 | 197 |
| 45.1[b] | 15.0 | 403 | 174 | 197 |
| 45.1[b,d] | 5.0 | 403 | 174 | 182 |
| 45.1[b,d] | 5.0 | 403 | 174 | 188 |

[a]Liposome samples (54% EPC, 45% CHOL, 1% MPE-DPPE) were prepared with different levels of coupled streptavidin by quenching the coupling mixture (20 mM final lipid concentration) with N-ethylmaleimide at various times.
[b]Streptavidin-liposomes were prepared at a final lipid concentration of 30 mM and an incubation period of 15 minutes.
[c]Streptavidin (50 ug) quenched with N-ethylmaleimide was extruded with liposomes (1 umole, 2.5 mM final lipid concentration) containing 1% MPB-DPPE.
[d]Extruded samples were kept on ice for 3 hours prior to QEL measurements.
[e]Extruded samples were frozen immediately after extrusion and thawed just prior to QEL measurements.

EXAMPLE 12

Blood Clearance of Protein-Liposome Conjugates

Figure 7:
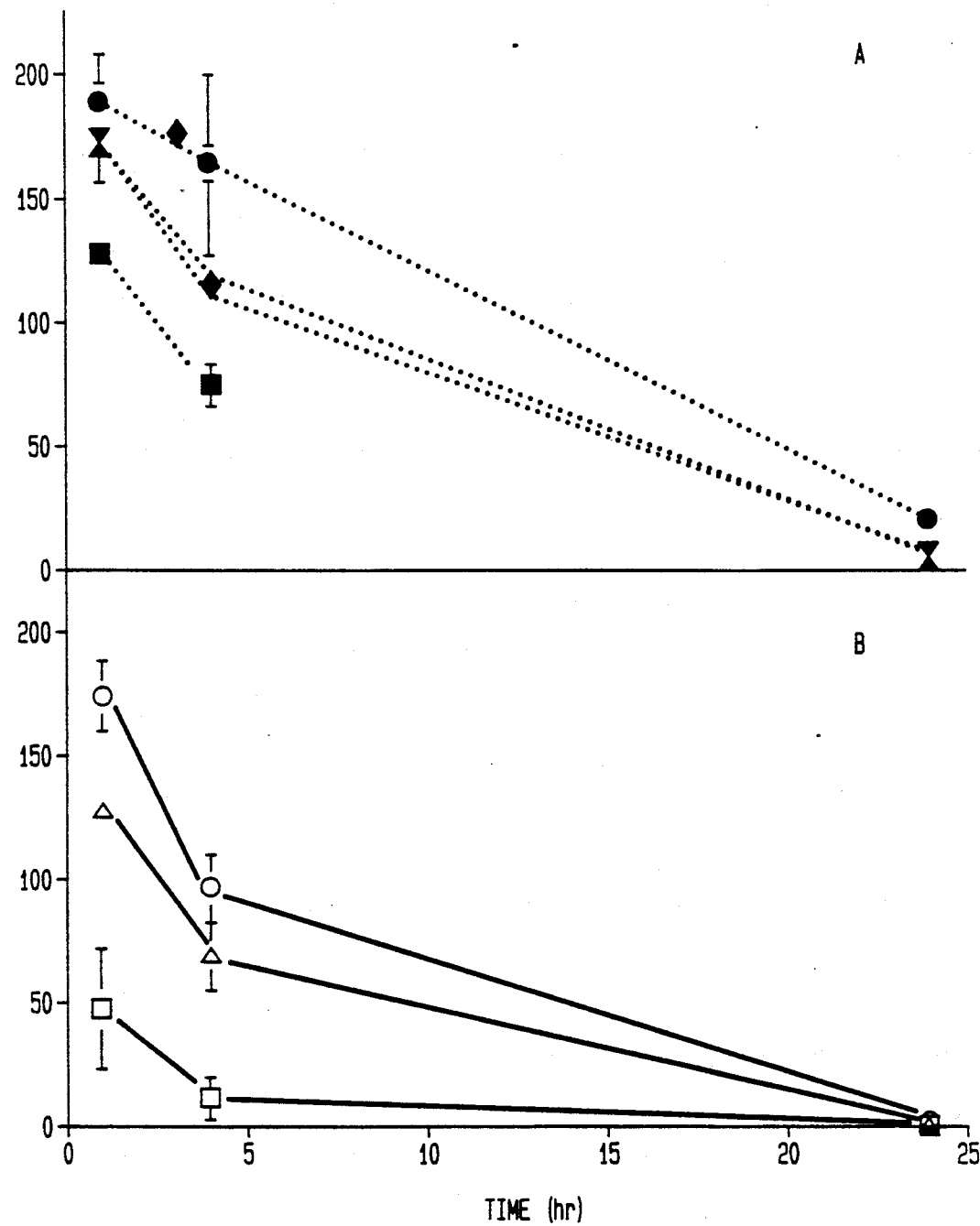
FIG. 7 is representative of the in vivo clearance rates of liposome preparations as described in Example 11. Streptavidin was coupled to liposomes (50 and 100 nm) at a final lipid concentration of 30 mM and incubation period of 15 minutes, quenched with N-ethylmaleimide for 2 hours followed by an overnight incubation with B-mercaptoethanol. Control liposomes containing MPB-PE were titrated to pH 7.5 and exchanged on sephadex G-50 equilibrated with HBS. EPC/CHOL liposomes were made up in HBS. Mice (4-8 mice per time point) were injected with lipid at a dose of 100 mg per kg. Plasma was prepared from EDTA whole blood at specific time points and aliquots were analysed by scintillation counting as described in the materials and methods section of Example 1. The size of extruded samples was determined by QELS. (A): EPC/CHOL, 125 nm (●); EPC/CHOL, 197 nm (■); MPB-PE liposomes, 170 nm (quenched ▼, unquenched ▲); (B): aggregated 100 nm streptavidin-liposomes, 530 nm (□); streptavidin-liposomes extruded through 100 nm filters, 187 nm (△) streptavidin-liposomes extruded through 50 nm, 139 nm (○).

Studies have shown that large liposomes are rapidly removed from the blood circulation when compared to small liposomes [See Hunt, A.C., Biochim. Biophys. Acta., 719, 450 (1982) and Sota, et al., Chem. Pharm. Bull., 34, 4244 (1986)]. Rapid clearance which was observed for targeted systems in vivo [See Wolff, et al., Biochim. Biophys. Acta., 802, 259 (1984) and Papahadjopoulos, et al., in "Annals of the New York Academy of Sciences", ed. R. L. Juliano, 507, 4035 (1988)]could partly be due to the aggregation of liposomes. To test this hypothesis, the time required for clearance from the blood of certain control liposome preparations (FIG. 7A) as well as aggregated and extruded streptavidin-liposome conjugates (FIG. 7B) in mice were therefore examined. Aggregated streptavidin-liposomes (530 nm in diameter as indicated by QELS) were cleared rapidly from the circulation; only 3% of the initial lipid dose remained in the circulation 4 hours after injection. Extrusion of these protein-vesicle conjugates through 50 or 100 nm polycarbonate filters resulted in preparations with size distributions of 139 and !87 nm respectively. Both of these preparations showed extended blood circulation times in vivo, with 48 and 32% of the initial dose remaining in circulation after 4 hours. When compared to EPC/CHOL vesicles of 125 nm size, the presence of covalently bound protein on liposomes of similar size (139 nm) enhanced the clearance of liposomes from the circulation (80 and 48% of EPC/CHOl vesicles remained in circulation after 4 hours versus 48 and 32% of protein-liposome conjugates). No significant difference in the circulation of MPB-PE liposomes (normal or quenched with B-mercaptoethanol, 170 nm in diameter) was observed when compared to EPC/-CHOL preparations of 197 nm in diameter.

As shown here, the extent of aggregation of the coupled liposomes significantly alters the blood clearance behavior of the conjugated preparations. As indicated, the aggregated streptavidin-liposomes (>530 nm in diameter) were rapidly removed from the circulation (<3 % remaining after 4 hours). In comparison, extended circulation times were obtained for extruded conjugates i.e., 32 and 48% of the initial lipid dose remained in circulation 4 hours post-injection for samples of 187 nm and 139 nm in diameter, respectively. The enhanced circulation times observed for smaller protein-liposome conjugates indicates that aggregation of the preparation is a major factor that determines the lifetimes of conjugates in vivo. It should be noted, however, that the clearance of protein-liposome conjugates from the blood was always greater than for control samples of similar size, indicating that the presence of protein on liposomes contributes to some extent to an enhanced clearance of liposomes from the circulation. The presence of the thiol reactive coupling lipid MPB-PE in liposomes does not significantly affect their in vivo clearance behavior when compared to EPC/-CHOL liposomes, suggesting that the binding of thiol-containing serum proteins does not affect the in vivo properties of liposomes.

EXAMPLE 13

Stability of Covalently Conjugated Liposomes In Vivo

The stability of covalently conjugated streptavidin-liposomes in vivo was demonstrated by the binding of biotin to liposome samples isolated from plasma 1 and 4 hours post injection (Table 2, below). A slight loss of biotin binding capacity of streptavidin-coupled liposomes was observed for samples isolated from plasma, which may have arisen from the absorption of serum components to the vesicles, the inactivation of streptavidin by proteolysis or the binding of endogenous biotin to the preparation.

TABLE 2

Stability of Streptavidin-Liposome Conjugates In Vivo
Streptavidin-Liposome - in ug Streptavidin/umol. Lipid Sample

| | Prior to Administration | After Administration 1 Hour | After Administration 4 hours |
|---|---|---|---|
| Aggregated (>530 nm) | 42.9 ± 0.1 | 43.1 ± 0.8 | 29.8 ± 0.8 |
| Extruded (187 nm) | 41.1 ± 2.8 | 35.4 ± 0.2 | 32.9 ± 0.3 |
| Extruded (139 nm) | 47.1 ± 0.5 | 44.5 ± 1.4 | 39.1 ± 0.6 |

The amount of streptavidin attached to liposomes was determined by the binding of $^{14}C$ biotin to lipid samples or pooled plasma samples from three mice, 1 and 4 hours post injection.

It will be understood by those skilled in the art that the foregoing description and examples are illustrative of practicing the present invention, but are in no way limiting. Variations of the detail presented herein ma be made without departing from the spirit and scope of the present invention.

We claim:

1. A composition comprising a stable, sized protein-liposome conjugate exhibiting an absence of aggregation wherein the conjugate comprises:
   1). the liposome comprising:
      a). at least about 90 ; mole percent of a liposome producing lipid;
      b). at least about 0.1 mole percent of a functionalized lipid; and
   2). a protein linked to said functionalized lipid in an amount equal to about 10 to about 100 protein molecules per liposome.

2. The protein-liposome conjugate according to claim 1 wherein said functionalized lipid comprises between about 0.25 and 1 mole percent of said conjugate.

3. The protein-liposome conjugate according to claim 1 wherein said protein is linked in an amount equal to about 55 to about 80 protein molecules per liposome vesicle.

4. The protein-liposome conjugate according to claim 1 wherein said functionalized lipid is selected from the group consisting of MPB-phosphatidylethanolamine, PDP-phosphatidylethanolamine and biotin-phosphatidylethanolamine.

5. The protein-liposome conjugate according to claim 1 wherein said protein is linked by covalent bonds to said functionalized lipid.

6. The protein-liposome conjugate according to claim 5 wherein said covalent bonds are disulfide bonds.

7. The protein-liposome conjugate according to claim 1 wherein said protein is selected from the group consisting of avidin, IgG, IgM, IgE, monoclonal antibodies and enzymes.

8. The protein-liposome conjugate according to claim 7 wherein said avidin is streptavidin.

9. The protein-liposome conjugate according to claim 8 wherein streptavidin is additionally coupled to biotinated protein.

10. The protein-liposome conjugate according to claim 1 wherein said protein is linked by non-covalent bonds to said functionalized lipid.

11. The protein-liposome conjugate according to claim 9 wherein said functionalized lipid is biotin-phosphatidylethanolamine.

12. The protein-liposome conjugate according to claim 1 ranging in size from about 75 nm to about 200 nm.

13. The protein-liposome conjugate according to claim 10 wherein said functionalized lipid contains biotin.

14. The protein-liposome conjugate according to claim 13 wherein said functionalized lipid is biotin-phosphatidylethanolamine.

15. The protein-liposome conjugate according to claim 1 containing a bioactive agent.

16. The protein-liposome conjugate according to claim 1 wherein said conjugate is dehydrated.

17. The protein-liposome conjugate according to claim 1 wherein said conjugate has a transmembrane potential.

18. The protein-liposome conjugate according to claim 1 wherein said conjugate contains a bioactive agent, has a transmembrane potential and is dehydrated.

19. The protein-liposome conjugate according to claim 15 wherein said bioactive agent is an antineoplastic agent.

20. The protein-liposome conjugate according to claim 7 wherein said protein is IgG.

21. The protein-liposome conjugate according to claim 7 wherein said protein is a monoclonal antibody.

22. A pharmaceutical composition comprising the protein-liposome conjugate according to claim 1 and a pharmaceutically acceptable carrier or diluent.

23. A method for producing a stable sized protein-liposome conjugate exhibiting an absence of aggregation comprising:
 1). forming a liposome vesicle comprising:
   a). at least about 90 mole percent of a liposome producing lipid; and
   b). at least about 0.1 mole percent of a functionalized lipid;
 2). linking a protein to said functionalized lipid wherein said protein is linked is an amount equal to about 10 to about 100 protein molecules per liposome vesicle to produce an aggregated protein liposome conjugate; and
 3). extruding said aggregated protein-liposome conjugate.

24. The method according to claim 23 wherein such functionalized lipid comprises between about 0.25 and 1 mole percent of said conjugate.

25. The method according to claim 23 wherein said protein is linked in an amount equal to about 55 to about 80 protein molecules per liposome vesicle.

26. The method according to claim 23 wherein said functionalized lipid is selected from the group consisting of MPB-phosphatidylethanolamine, PDP-phosphatidylethanolamine and biotin-phosphatidylethanolamine.

27. The method according to claim 23 wherein said protein is linked by covalent bonds to said functionalized lipid.

28. The method according to claim 27 wherein said covalent bonds are disulfide bonds.

29. The method according to claim 23 wherein said protein is selected from the group consisting of avidin, IgG, IgM, IgE, monoclonal antibodies and enzymes.

30. The method according to claim 29 wherein said avidin is streptavidin.

31. The method according to claim 30 wherein streptavidin is additionally coupled to biotinated protein.

32. The method according to claim 23 wherein said protein is linked by non-covalent bonds to said functionalized lipid.

33. The method according to claim 32 wherein said functionalized lipid is biotin-phosphatidylethanolamine.

34. The method according to claim 23 wherein the liposomes range in size from about 75 nm to about 200 nm.

35. The method according to claim 23 wherein said conjugate is dehydrated after said extrusion step.

36. The method according to claim 29 wherein said protein is IgG.

37. The method according to claim 29 wherein said protein is a monoclonal antibody.

38. The method according to claim 23 wherein said extrusion step (step 3) is performed through polycarbonate filters ranging in pore size from about 30 nm to about 11 nm.

39. The method according to claim 38 wherein said extrusion step is performed under high pressure.

40. A method for loading a protein-liposome conjugate with a bioactive agent, said protein-liposome conjugate being surrounded by an external aqueous medium, comprising the steps of:
 (a) producing a transmembrane potential in a protein-liposome conjugate according to claim 1 with an orientation which will load the bioactive agent into the protein-liposome conjugate; and
 (b) admixing the bioactive agent with the protein-liposome conjugate in the external aqueous medium.

41. The method according to claim 40 wherein said bioactive agent is an anti-neoplastic agent.

42. The method according to claim 41 wherein said anti-neoplastic agent is selected from the group consisting of daunorubicin, doxirubicin, vinblastine, and pharmaceutically acceptable salts and derivatives thereof.

43. The method according to claim 40 comprising the additional step of dehydrating the resulting proteinliposome conjugate of step (b) to obtain a dehydrated composition.

44. The method according to claim 40 wherein said protein is avidin.

45. The method according to claim 44 wherein said avidin is streptavidin.

46. The method according to claim 40 wherein said protein is IgG.

47. The method according to claim 40 wherein said protein is a monoclonal antibody.

48. The method according to claim 40 wherein said protein-liposome conjugate is produced by a method which comprises 1) forming a liposome vesicle comprising: a) at least about 90 mole percent of a liposome producing lipid; and b) at least about 0.1 mole percent of a functionalized lipid; 2) linking a protein to said functionalized lipid wherein said protein is linked in an amount equal to about 10 to about 100 protein molecules per liposome vesicle to produce an aggregated protein-liposome conjugate; and 3) extruding said aggregated protein-liposome conjugate.

49. A method for storing the protein-liposome conjugate according to claim 1 which comprises the steps of: a) dehydrating such to obtain a dehydrated composition; and b) storing the dehydrated composition.

50. The method according to claim 49 wherein the composition is dehydrated in the presence of a protective sugar.

51. The method according to claim 50 wherein the protective sugar is a disaccharide.

52. The method according to claim 51 wherein said disaccharide is selected from the group consisting of trehalose, maltose, sucrose, glucose, lactose and dextran.

53. The method according to claim 51 wherein said disaccharide is trehalose.

54. The method according to claim 49 wherein said protein-liposome conjugate has a transmembrane potential.

55. The method according to claim 49 wherein said protein-liposome conjugate contains a bioactive agent.

56. The method according to claim 55 wherein said bioactive agent is an antineoplastic agent.

57. A method for targeting the delivery of a bioactive agent to a subject comprising administering a protein-liposome conjugate according to claim 15 to said subject.

58. The method according to claim 57 wherein said protein is avidin.

59. The method according to claim 58 wherein said avidin is streptavidin.

60. The method according to claim 57 wherein said protein is IgG.

61. The method according to claim 57 wherein said protein is a monoclonal antibody.

62. The method according to claim 57 wherein said bioactive agent is an anti-neoplastic agent and said subject is a human patient.

63. A method for assaying a sample for an antibody comprising contacting a protein-liposome conjugate according to claim 1 with a sample.

64. The method according to claim 63 wherein said protein is avidin.

65. The method according to claim 64 wherein said avidin is streptavidin.

66. The method according to claim 63 wherein said protein is IgG.

67. The method according to claim 63 wherein said protein is a monoclonal antibody.

68. A stable sized protein-liposome conjugate exhibiting an absence of aggregation produced by the method comprising
   1). forming an aggregated protein-liposome conjugate comprising a liposome vesicle comprising:
      a). at least about 90 mole percent of a liposome producing lipid;
      b). at least about 0.1 mole percent of a functionalized lipid; and
      c). a protein linked to said functionalized lipid in an amount equal to about 10 to about 100 protein molecules per liposome vesicle; and
   2). extruding said aggregated protein-liposome conjugate.

* * * * *